(12) United States Patent
Messing et al.

(10) Patent No.: US 6,376,467 B1
(45) Date of Patent: Apr. 23, 2002

(54) USE OF INHIBITORS OF PROTEIN KINASE C EPSILON TO TREAT PAIN

(75) Inventors: Robert O. Messing, Foster City; Jon D. Levine, San Francisco, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/347,370

(22) Filed: Jul. 6, 1999

Related U.S. Application Data
(60) Provisional application No. 60/103,763, filed on Oct. 9, 1998, and provisional application No. 60/097,755, filed on Jul. 6, 1998.

(51) Int. Cl.$^7$ .......................... A61K 38/08; A61K 38/00
(52) U.S. Cl. ............................ 514/15; 424/9.2; 514/16; 514/238.2; 514/247; 514/455; 514/459; 514/475; 514/510; 514/544
(58) Field of Search .......................... 435/194; 424/9.2; 514/14, 15, 16, 238.2, 255, 315, 331, 455, 459, 471, 475, 480, 510, 541, 544, 561, 567, 569, 564, 617, 618, 619, 620, 621, 625, 637, 647, 656, 680

(56) References Cited

U.S. PATENT DOCUMENTS

| | | | |
|---|---|---|---|
| 5,141,957 A | * 8/1992 | Jiang et al. | 514/510 |
| 5,204,370 A | * 4/1993 | Jiang et al. | 514/475 |
| 5,216,014 A | * 6/1993 | Jiang et al. | 514/455 |
| 5,270,310 A | * 12/1993 | Bell et al. | 514/238.2 |
| 5,292,737 A | * 3/1994 | Defauw | 514/247 |
| 5,344,841 A | * 9/1994 | Jiang et al. | 514/459 |
| 5,360,818 A | * 11/1994 | Jiang et al. | 514/459 |
| 5,432,198 A | * 7/1995 | Jagdmann, Jr. | 514/544 |
| 5,519,003 A | 5/1996 | Mochly-Rosen et al. | 514/16 |
| 5,565,454 A | * 10/1996 | Cincotta | 514/250 |
| 5,716,968 A | * 2/1998 | Driedger et al. | 514/323 |
| 5,783,405 A | * 7/1998 | Mochly-Rosen et al. | 435/15 |
| 5,800,385 A | * 9/1998 | Demopolus et al. | 604/49 |
| 5,919,826 A | * 7/1999 | Caruso | 514/629 |

FOREIGN PATENT DOCUMENTS

| | | |
|---|---|---|
| WO | WO 97/15575 | 5/1997 |

OTHER PUBLICATIONS

Wyngaarden et al, eds. Cecil Textbook of Medicine, 19th ed. Philadelphia: W.B. Saunders Co. vol. 2, pp. 2244–2245, 1992.*

Gekeler et al. Effects of the selective bisindolylmaleimide . . . Br. J. Cancer, vol. 74, No. 6, pp. 897–905, Sep. 1996.*

Schaap et al. Expression, Purification, and Characterization . . . J. Biol. Chem. vol. 265, No. 13, pp. 7301–7307, May 5, 1990.*

Ahlgren et al., "Increased Responsiveness of Sensory Neurons in the Saphenous Nerve of the Streptozotocin–Diabetic Rat," *Journal of Neurophysiology*, 68(6):2077–2085, (1992).

Ahlgren et al., "Mechanical Hyperalgesia in Streptozotocin–Diabetic Rats," *Neuroscience*, 52(4):1049–1055, (1993).

Aley et al., "Different Mechanisms Mediate Development and Expression of Tolerance and Dependence for Peripheral μ–Opioid Antinociception in Rat," *The Journal of Neuroscience*, 17(20):8018–8023, (1997).

(List continued on next page.)

Primary Examiner—Jeffrey E. Russel
(74) Attorney, Agent, or Firm—Cooley Godward LLP

(57) ABSTRACT

The role of the ε isozyme of protein kinase C ("PKCε") in pain perception, particularly hyperalgesia, methods of lessening pain through administration of inhibitors of PKCε, methods of identifying compounds that modulate pain, and pharmaceutical compositions comprising an inhibitor of PKCε and PKCε-independent analgesic agent are disclosed.

4 Claims, 11 Drawing Sheets

OTHER PUBLICATIONS

Aley et al., "Vincristine Hyperalgesia in the Rat: A Model of Painful Vincristine Neuropathy in Humans," *Neuroscience*, 73(1):259–265, (1996).

Baccaglini et al., "Some rat sensory neurons in culture express characteristics of differentiated pain sensory cells," *Proc. Natl. Acad. Sci. USA*, 80:594–598, (1983).

Bjorkman, "Central antinociceptive effects of non–steroidal anti–inflammatory drugs and paracetamol," *Acta Anaesthesiol. Scand.*, 39(103):2–44, (1995).

Choi et al., "Effect of adrenergic receptor activation on post–herpetic neuralgia pain and sensory disturbances," *Pain*, 69:55–63, (1997).

England et al., "$PGE_2$ modulates the tetrodotoxin–resistant sodium current in neonatal rat dorsal root ganglion neurones via the cyclic AMP–protein kinase A cascade," *Journal of Physiology*, 495(2):429–440, (1996).

Eriksson et al., "Effect of Epinephrine Infusion on Chest Pain in Syndrome X in the Absence of Signs of Myocardial Ischemia," *Am. J. Cardiol.*, 75:241–245, (1995).

Ferreira et al., "Interleukin–1β as a potent hyperalgesic agent antagonized by a tripeptide analogue," *Nature*, 334:698–700, (1988).

Gold et al., "Co–Expression of Nociceptor Properties in Dorsal Root Ganglion Neurons from the Adult Rat in–vitro," *Neuroscience*, 71(1):265–275, (1996).

Gold et al., "Hyperalgesic agents increase a tetrodotoxin–resistant $Na^+$ current in nociceptors," *Proc. Natl. Acad. Sci. USA*, 93:1108–1112, (1996).

Goodnight et al., "Selective Involvement of Protein Kinase C Isozymes in Differentiation and Neoplastic Transformation," *Advances in Cancer Research*, 64:159–209, (1994).

Khasar et al., "Is There More Than One Prostaglandin E Receptor Subtype Mediating Hyperalgesia in the Rat Hindpaw?," *Neuroscience*, 64(4):1161–1165, (1995).

Kinnman et al., "Sensory and Sympathetic Contributions to Nerve Injury–Induced Sensory Abnormalities in the Rat," *Neuroscience*, 64(3):751–767, (1995).

Levine et al., "Noradrenaline hyperalgesia is mediated through interaction with sympathetic postganglionic neurone terminals rather than activation of primary afferent nociceptors," *Nature*, 323:158–160, (1986).

Macfarlane et al., "Activation of β–Isozyme of Protein Kinase C (PKCβ) Is Necessary and Sufficient for Phorbol Ester–induced Differentiation of HL–60 Promyelocytes," *The Journal of Biological Chemistry*, 269(6):4327–4331, (1994).

Nishizuka, "Studies and Perspectives of Protein Kinase C," *Science*, 233:305–312, (1986).

Ouseph et al., "Multiple Second Messenger Systems Act Sequentially to Mediate Rolipram–Induced Prolongation of Prostaglandin $E_2$–Induced Mechanical Hyperagesia in the Rat," *Neuroscience*, 64(3):769–776, (1995).

Pitchford et al., "Prostaglandins sensitize nociceptors in cell culture," *Neuroscience Letters*, 132:105–108, (1991).

Powell et al., "Protein kinase C isozymes ε and α in murine erythroleukemia cells," *Proc. Natl. Acad. Sci. USA*, 89:147–151, (1992).

Selbie et al., "Molecular Cloning and Characterization of PKC1, an Atypical Isoform of Protein Kinase C Derived from Insulin–secreting Cells," *The Journal of Biological Chemistry*, 268(32):24296–24302, (1993).

Taiwo et al., "Characterization of Distinct Phospholipases Mediating Bradykinin and Noradrenaline Hyperalgesia," *Neuroscience*, 39(2):523–531, (1990).

Taiwo et al., "Further Confirmation of the Role of Adenyl Cyclase and of cAMP–Dependent Protein Kinase in Primary Afferent Hyperalgesia," *Neuroscience*, 44(1):131–135, (1991).

Takai et al., "Role of Protein Kinase C in Transmembrane Signaling," *Journal of Cellular Biochemistry*, 29:143–155, (1985).

Toullec et al., "The Bisindolylmaleimide GF 109203X Is a Potent and Selective Inhibitor of Protein Kinase C," *The Journal of Biological Chemistry*, 266(24):15771–15781, (1991).

Valverde et al., "Molecular cloning and characterization of protein kinase D: A target for diacylglycerol and phorbol esters with a distinctive catalytic domain," *Proc. Natl. Acad. Sci. USA*, 91:8572–8576, (1994).

Vinegar et al., "Quantitative Comparison of the Analgesic and Anti–Inflammatory Activities of Aspirin, Phenacetin and Acetaminophen in Rodents," *European Journal of Pharmacology*, 37:23–30, (1976).

Ward et al., "Relative Involvement of Mu, Kappa and Delta Receptor Mechanisms in Opiate–Mechanisms in Opiate–Mediated Antinociception in Mice," *The Journal of Pharmacology and Experimental Therapeutics*, 224(3):525–530, (1983).

West et al., "Transient Permeabilization Induced Osmotically in Membrane Vesicles from Torpedo Electroplax: A Mild Procedure for Trapping Small Molecules," *Biochemistry*, 19:4418–4423, (1980).

Niemegger, et al., "Suprofen, A Potent Antagonist of Acetic Acid–Induced Writhing in Rats," *Arzneimittelforschung*, 25:1505–1509, (1975).

Ahlgren et al., "Protein Kinase C Inhibitors Decrease Hyperalgesia and C–Fiber Hyperexcitability in the Streptozotocin–Diabetic Rat," *J. Neurophysiol.*, 72(2):684–692, (1994).

Cesare et al., "Specific Involvement of PKC–ε in Sensitization of the Neuronal Response to Painful Heat," *Neuron*, 23:617–624, (1999).

Coderre, "Contribution of Protein Kinase C to Central Sensitization and Persistent Pain Following Tissue Injury," *Neuroscience Letters*, 140:181–184, (1992).

Coderre et al., "Intracellular Messengers Contributing to Persistent Nociception and Hyperalgesia Induced by L–Glutamate and Substance P in the Rat Formalin Pain Model," *Eur. J. Neuroscience*, 6:1328–1334, (1994).

Hattori, "Role of Spinal N–type Ca Channel and Protein Kinase C Activities in Modulating Hyperalgesia. Determination of Spinal Amino Acid Release and Pain Related Response," *Database Chemical Abstracts Service*, AN: 126:5425 (1996).

Hundle et al., "An Inhibitory Fragment Derived from Protein Kinase Cε Prevents Enhancement of Nerve Growth Factor Responses by Ethanol and Phorbol Esters," *J. Biol. Chem.*, 272(23):15028–15035, (1997).

Hundle et al., "Overexpression of ε–Protein Kinase C Enhances Nerve Growth Factor–Induced Phosphorylation of Mitogen–activated Protein Kinases and Neurite Outgrowth," *J. Biol. Chem.*, 270(50):30134–30140, (1995).

Johnson et al., "A Protein Kinase C Translocation Inhibitor as an Isozyme–selective Antagonist of Cardiac Function," *J. Biol. Chem.*, 271(40):24962–24966, (1996).

Khasar et al., "A Novel Nociceptor Signaling Pathway Revealed in Protein Kinase Cε Mutant Mice," *Neuron*, 24:253–260, (1999).

Khasar et al., "Epinephrine Produces a β–Adrenergic Receptor–Mediated Mechanical Hyperalgesia and In Vitro Sensitization of Rat Nociceptors," *J. Neurophysiol.*, 81(3):1104–1112, (1999).

Lewin et al., "Nerve Growth and Nociception," *TINS*, 16(9):353–359, (1993).

Lewin et al., "Nerve Growth Factor–Induced Hyperalgesia in the Neonatal and Adult Rat," *J. Neuroscience*, 13(5):2136–2148, (1993).

Lin et al., "Inhibition of Primate Spinothalamic Tract Neurons by Spinal Glycine and GABA is Reduced During Central Sensitization," *J. Neurophysiol.*, 76(2):1005–1014, (1996).

Mao, "Excitatory Central Mechanisms of Post–Injury Neuropathic Pain," *Database Dissertation Abstracts*, AN: 01237083 (1992).

Mao et al., "Increases in Protein Kinase C Gamma Immunoreactivity in the Spinal Cord Dorsal Horn of Rats with Painful Mononeuropathy," *Neuroscience Letters*, 198(2):75–78, (1995).

McGuirk et al., "G–Protein Mediation in Nociceptive Signal Transduction: An Investigation into the Excitatory Action of Bradykinin in a Subpopulation of Cultured Rat Sensory Neurons," *Neuroscience*, 49(1):117–128, (1992).

Munro et al., "Evidence for a Role of Protein Kinase C in the Sustained Activation of Rat Dorsal Horn Neurons Evoked by Cutaneous Mustard Oil Application," *Neuroscience Letters*, 170:199–202, (1994).

Ohsawa et al., "Modulation of the Formalin–Induced Nociceptive Response by Diabetes: Possible Involvement of Protein Kinase C," *Brain Research*, 803:198–203, (1998).

Sluka et al., "Capsaicin–induced Sensitization of Primate Spinothalamic Tract Cells is Prevented by a Protein Kinase C Inhibitor," *Brain Research*, 772:82–86, (1997).

Sluka et al., "The Effects of G–Protein and Protein Kinase Inhibitors on the Behavioral Responses of Rats to Intradermal Injection of Capsaicin," *Pain*, 71:165–178, (1997).

Yashpal et al., "Noxious Thermal and Chemical Stimulation Induce Increases in $^3$H–Phorbol 12,13–Dibutyrate Binding in Spinal Cord Dorsal Horn As Well As Persistent Pain and Hyperalgesia, Which is Reduced by Inhibition of Protein Kinase C," *J. Neuroscience*, 15(5):3263–3272, (1995).

Berra et al., "Protein Kinase C ξ Isoform is Critical for Mitogenic Signal Transduction," *Cell*, 74:555–563, (1993).

Boland et al., "Inhibition by Bradykinin of Voltage–Activated Barium Current in a Rat Dorsal Root Ganglion Cell Line: Role of Protein Kinase C," *The Journal of Neuroscience*, 11(4):1140–1149, (1991).

Cesare et al., "A novel heat–activated current in nociceptive neurons and its sensitization by bradykinin," *Proc. Natl. Acad. Sci. USA*, 93:15435–15439, (1996).

Chakravarthy et al., "The Direct Measurement of Protein Kinase C (PKC) Activity in Isolated Membranes Using a Selective Peptide Substrate," *Analytical Biochemistry*, 196:144–150, (1991).

Csukai et al., "The Coatomer Protein β'–COP, a Selective Binding Protein (RACK) for Protein Kinase Cε," *J. Biol. Chem.*, 272(16):29200–29206, (1997).

Gruber et al., "Increased Expression of Protein Kinase C Plays a Key Role in Retinoic Acid–induced Melanoma Differentiation," *The Journal of Biological Chemistry*, 267(19):13356–13360, (1992).

Johannes et al., "PKCu Is a Novel, Atypical Member of the Protein Kinase C Family," *The Journal of Biological Chemistry*, 269(8):6140–6148, (1994).

Kitano et al., "Assay and Purification of Protein Kinase C," *Methods in Enzymology*, 124(24):349–352, (1986).

Lehel et al., "A Chemiluminescent Microtiter Plate Assay for Sensitive Detection of Protein Kinase Activity," *Analytical Biochemistry*, 244:340–346, (1997).

Leng et al., "Excitation and sensitization of the heat response induced by a phorbol ester in canine visceral polymodal receptors studied in vitro," *Neuroscience Letters*, 206:13–16, (1996).

Lin et al., "Generation of PKCε Knockout Mice," *Signal Transduction and Lipid Second Messengers III*, p. 65, Abstract No. 320, (1998).

Lin et al., "Using Knockout Mice to Study the Role of PKCε in Neuronal Development," *Society for Neuroscience*, p. 594, Abstract No. 240.4, (1997).

Messing et al., "Chronic Ethanol Exposure Increases Levels of Protein Kinase C δ and ε and Protein Kinase C–mediated Phosphorylation in Cultured Neural Cells," *The Journal of Biological Chemistry*, 266(34):23428–23432, (1991).

Messing et al., "Protein Kinase C Participates in Up–Regulation of Dihydropyridine–Sensitive Calcium Channels by Ethanol," *Journal of Neurochemistry*, 55(4):1383–1389 (1990).

Nishizuka "Intracellular Signaling by Hydrolysis of Phospholipids and Activation of Protein Kinase C," *Science*, 258:607–614, (1992).

\* cited by examiner

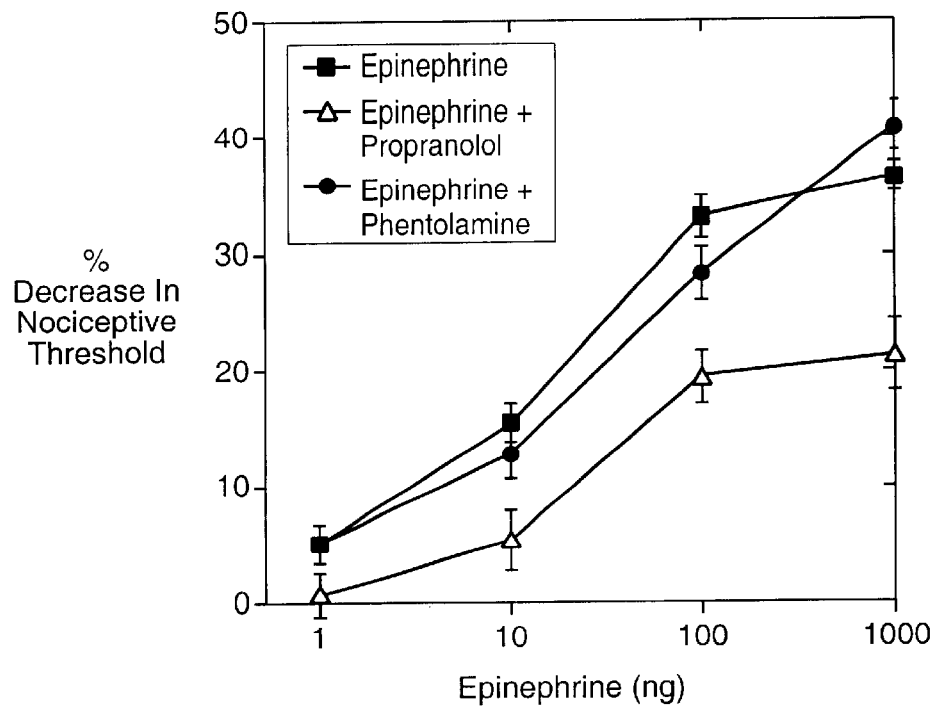
FIG._1A
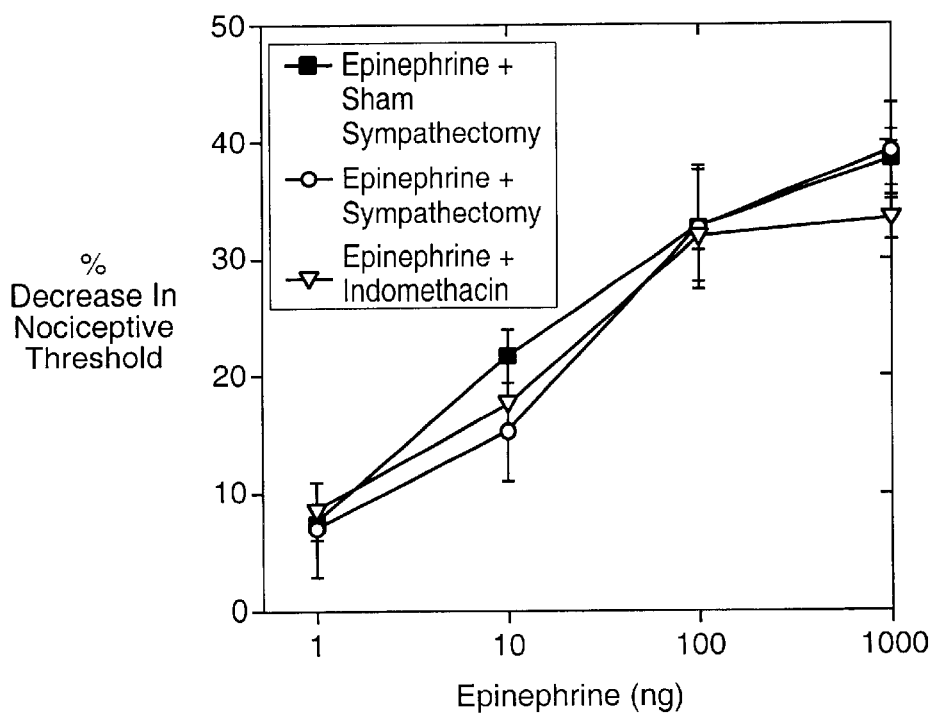
FIG._1B

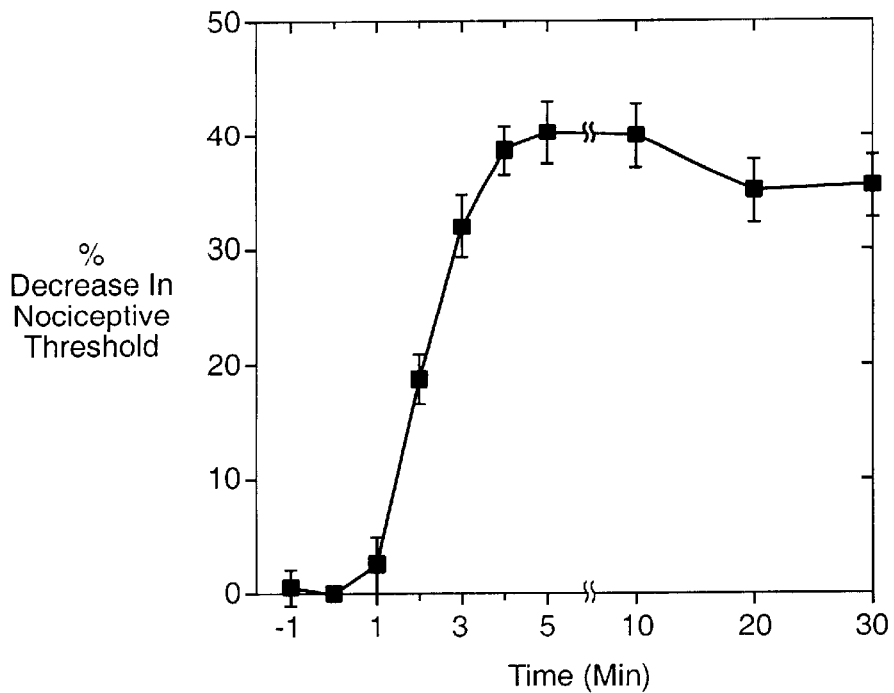
FIG._2A
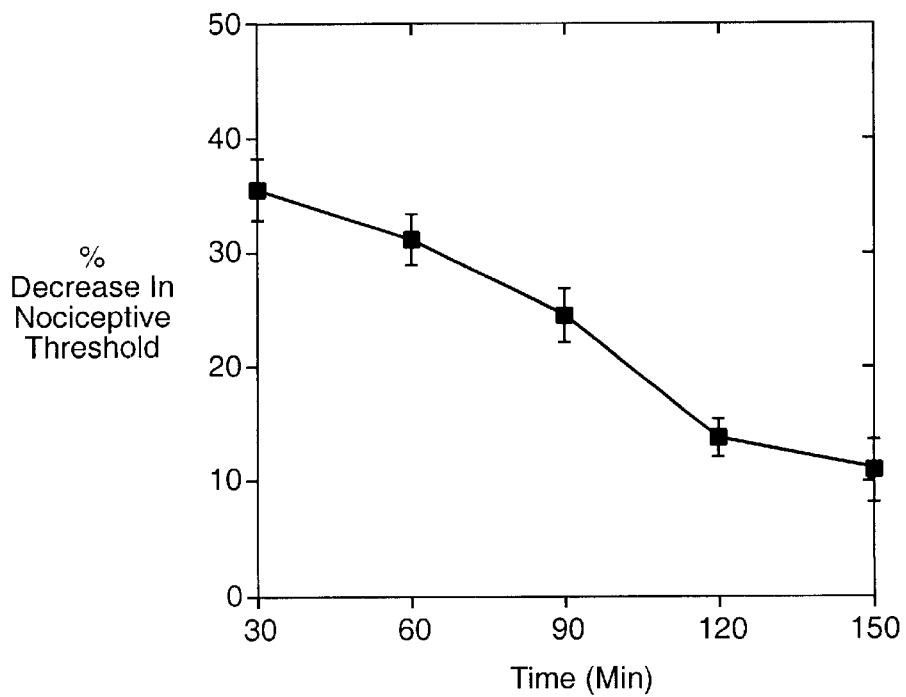
FIG._2B

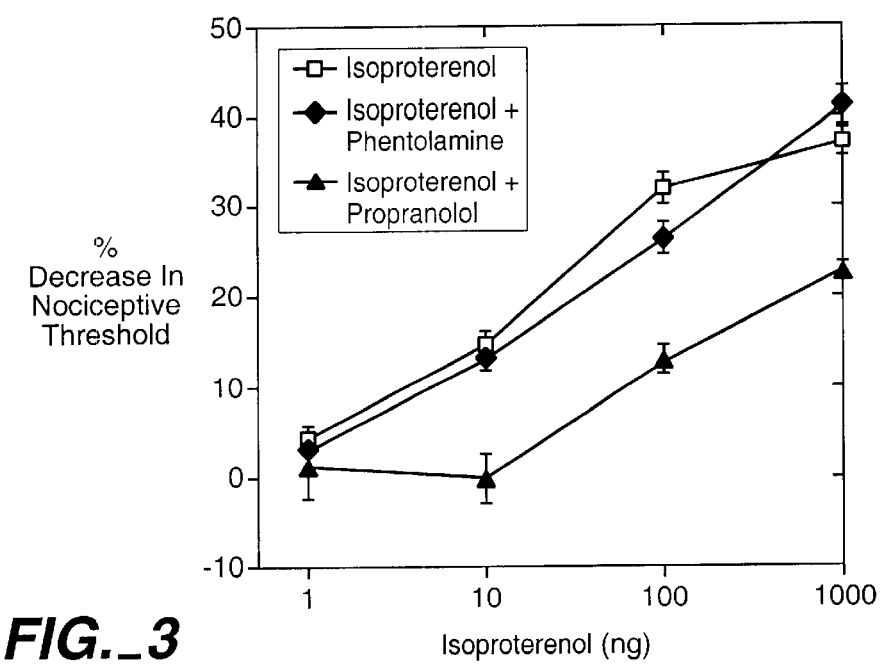
FIG._3
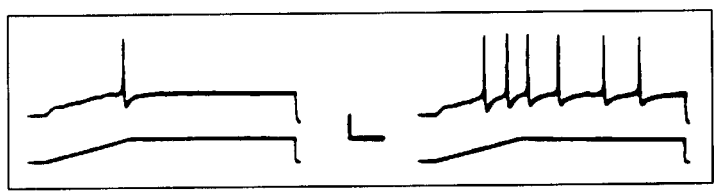
FIG._4A
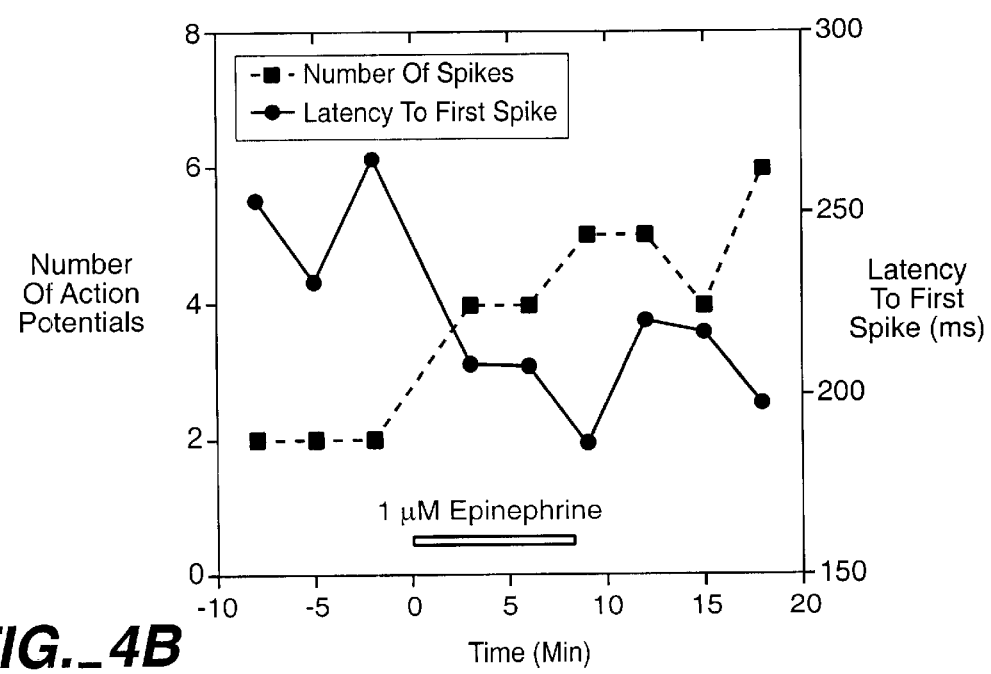
FIG._4B

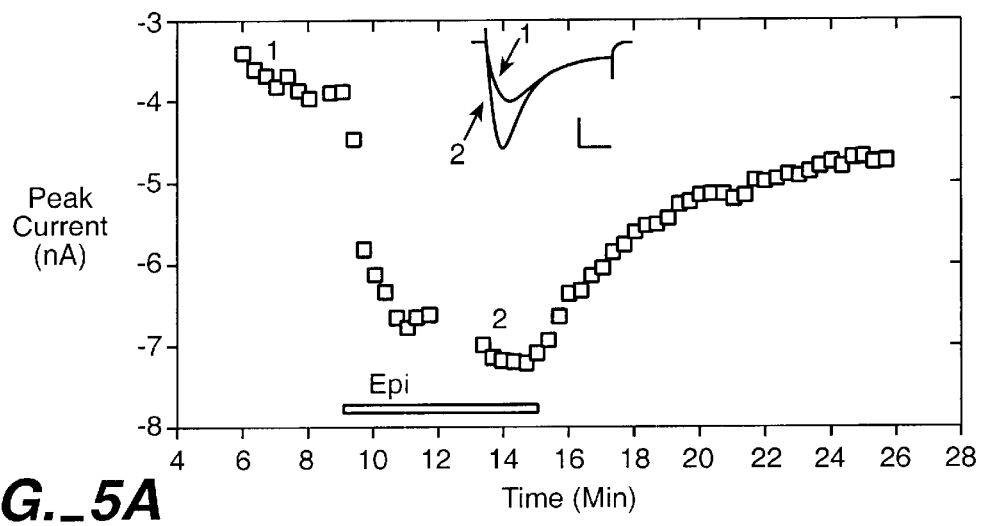
FIG._5A
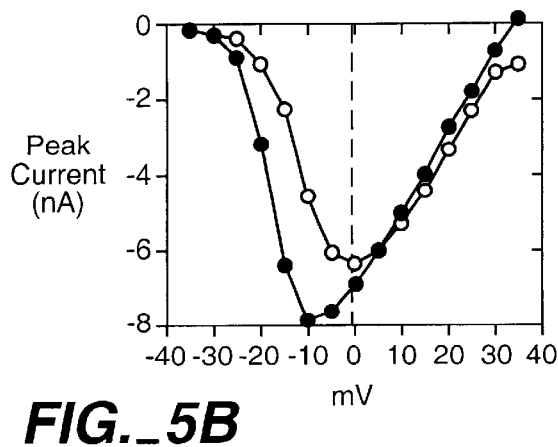
FIG._5B
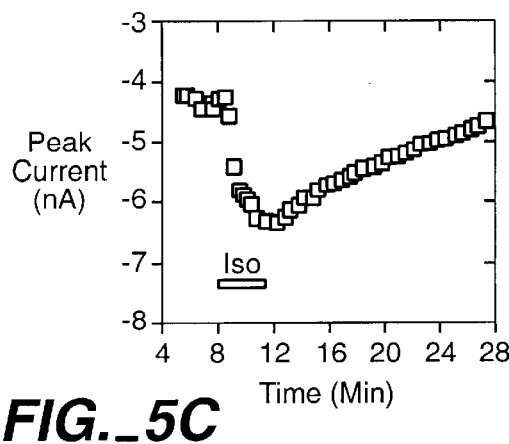
FIG._5C
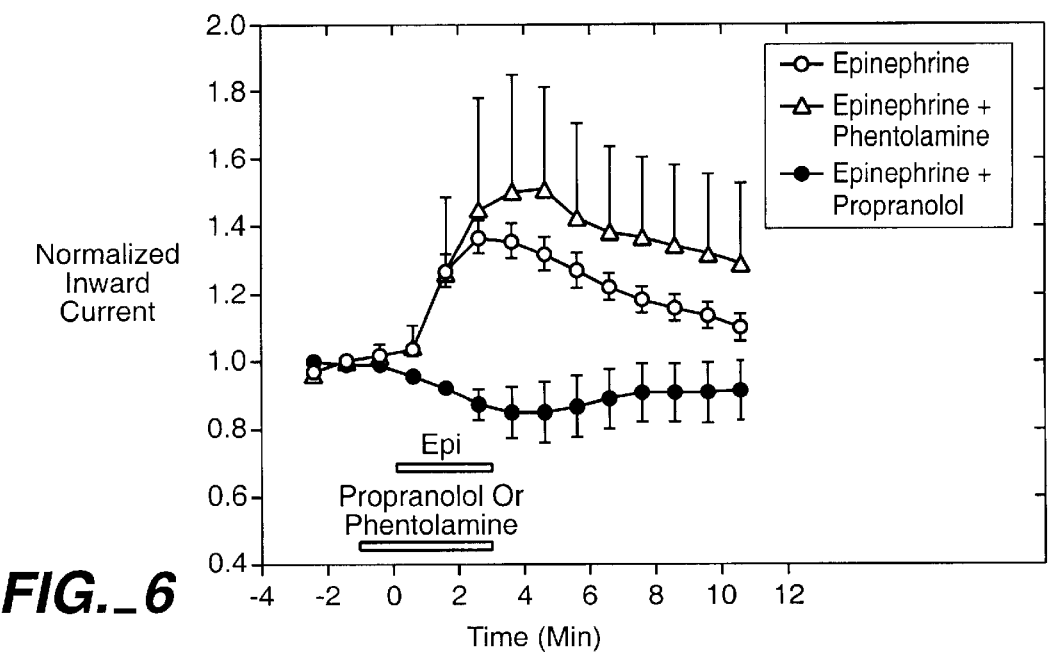
FIG._6

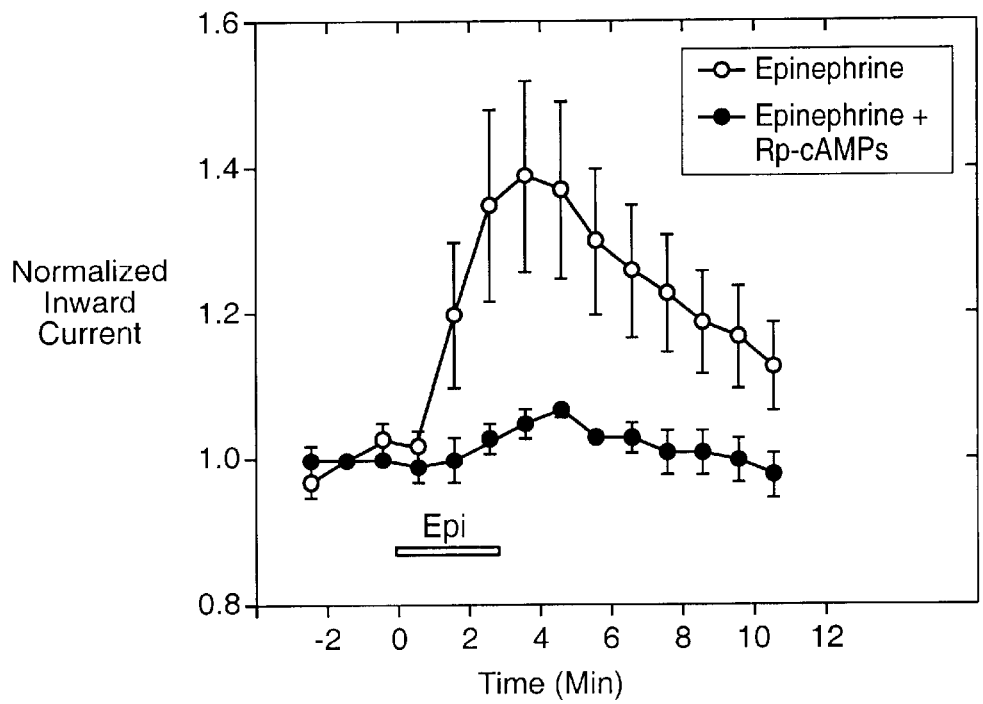
FIG._7
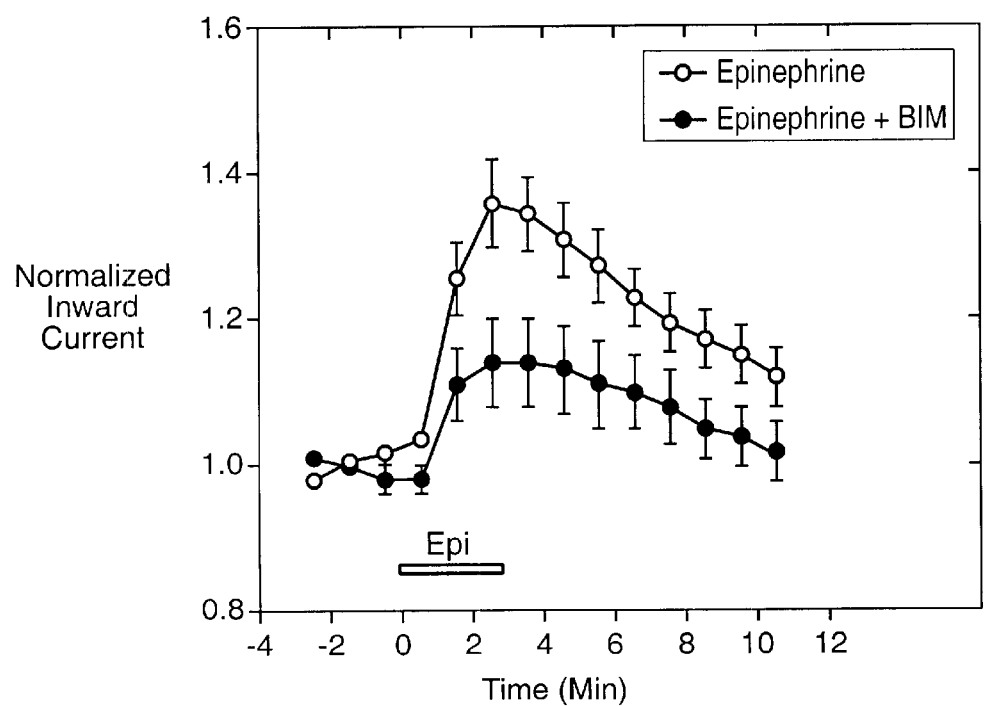
FIG._8

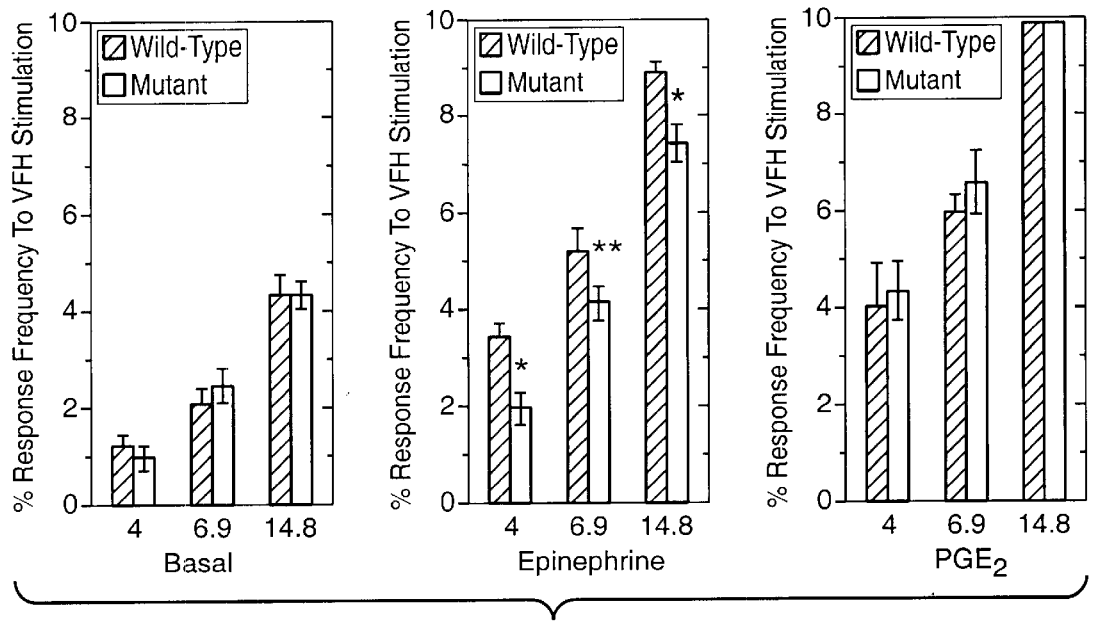
FIG._9A
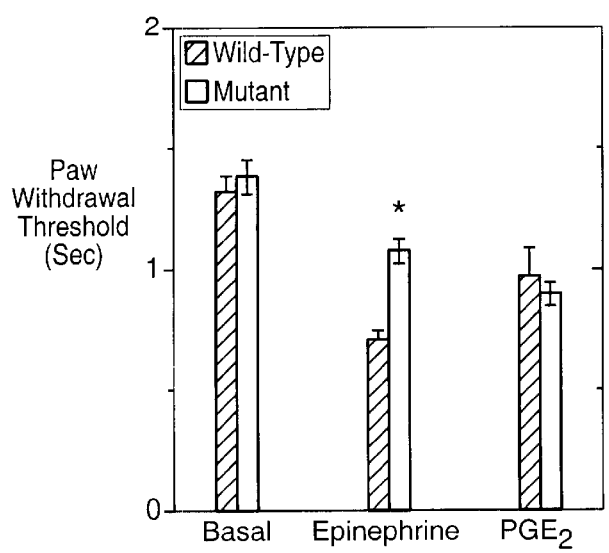
FIG._9B
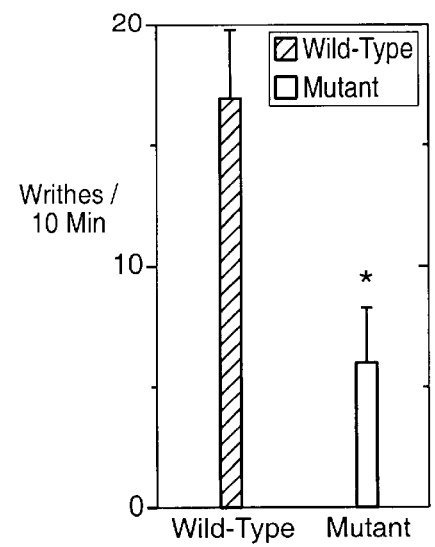
FIG._9C

 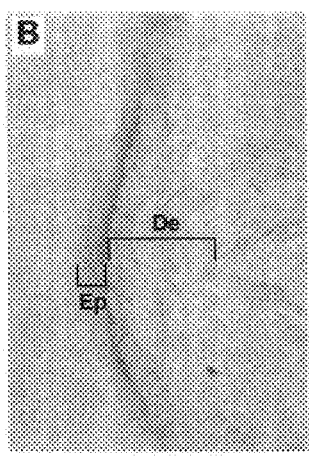 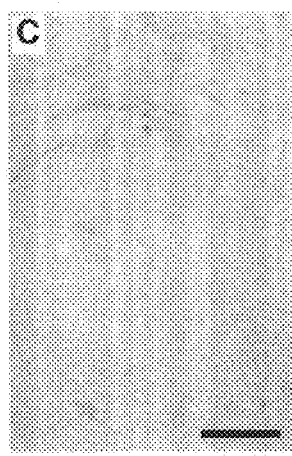
FIG._10A     FIG._10B     FIG._10C

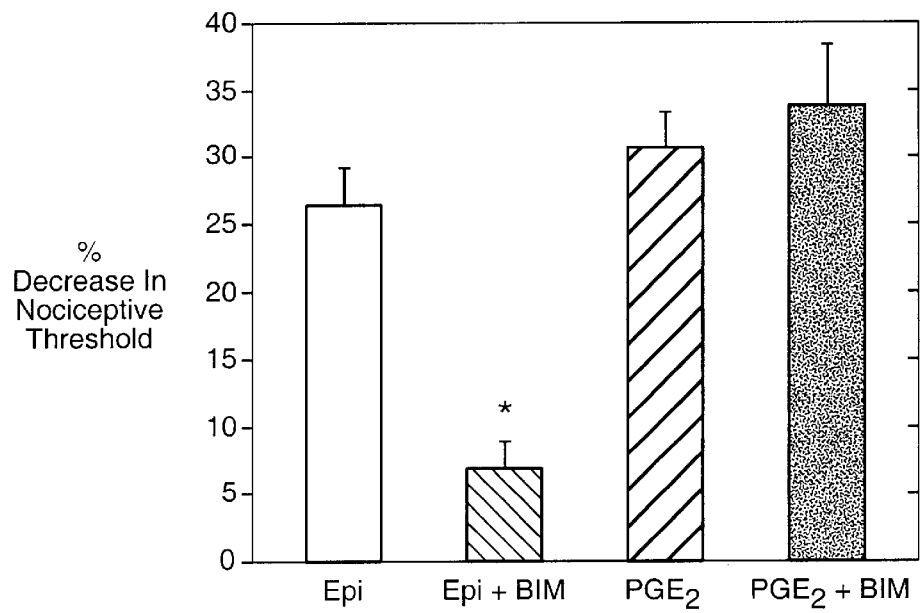
FIG._10D
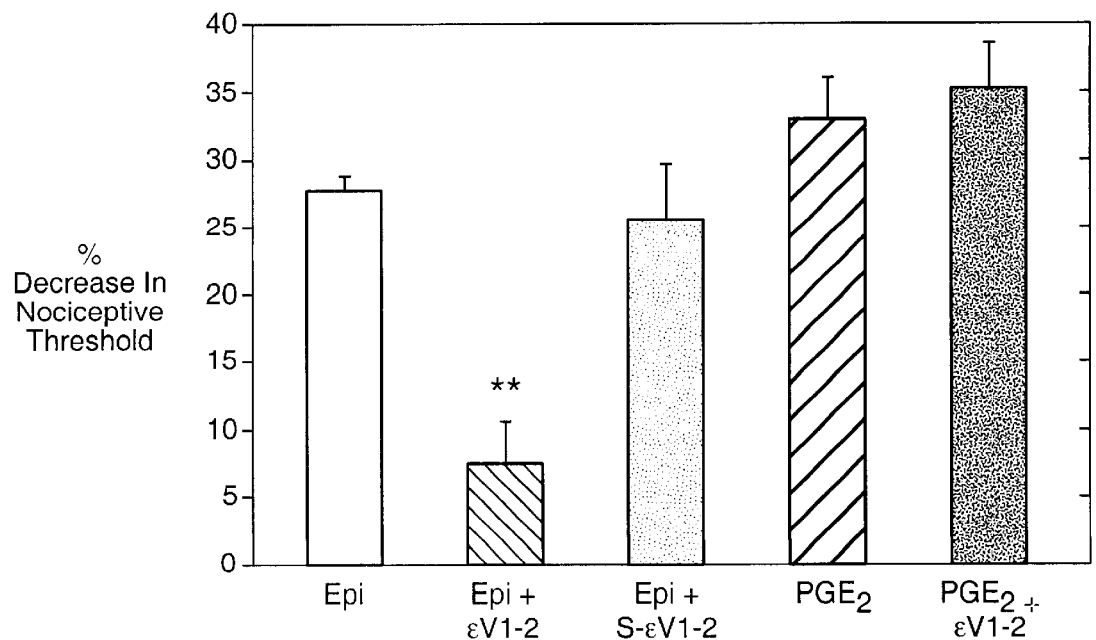
FIG._10E

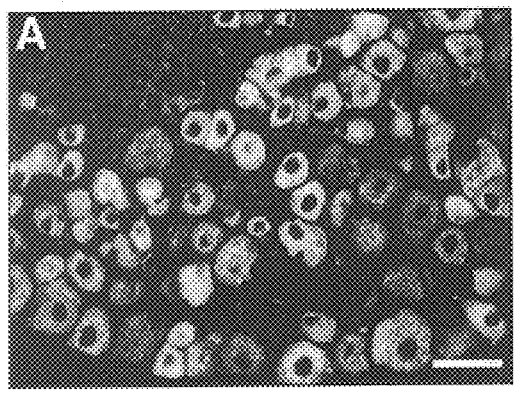
*FIG._11A*
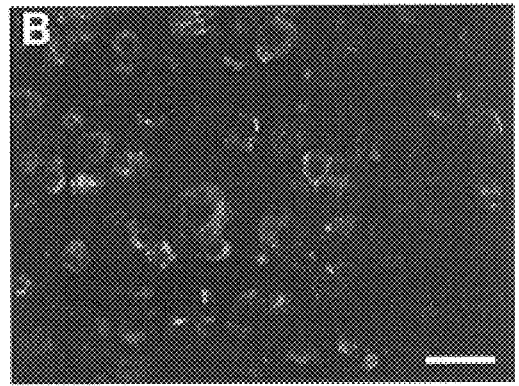
*FIG._11B*
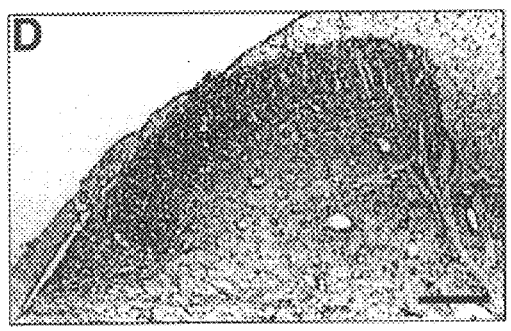
*FIG._11D*
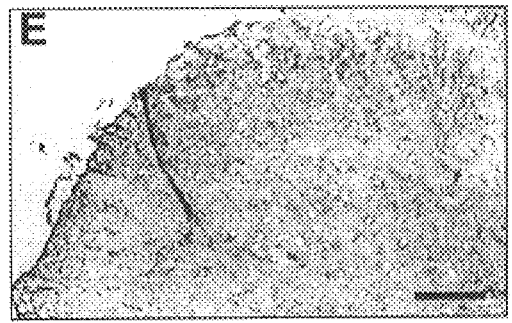
*FIG._11E*

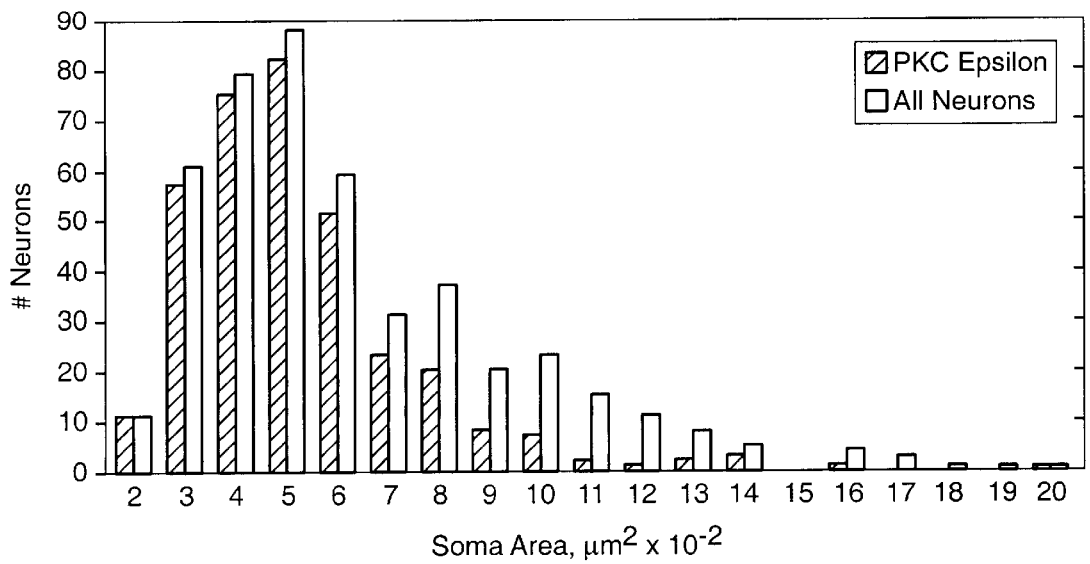
FIG._11C
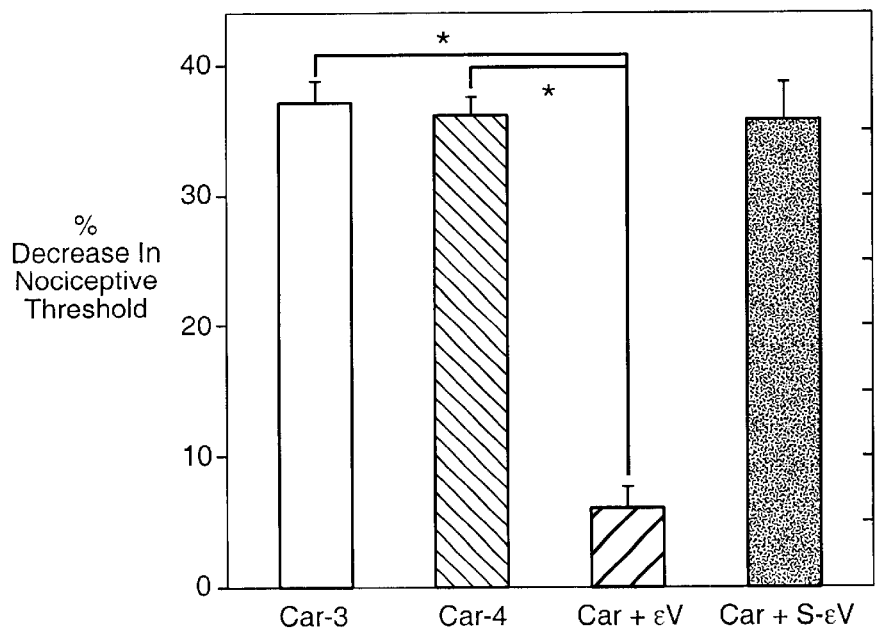
FIG._13

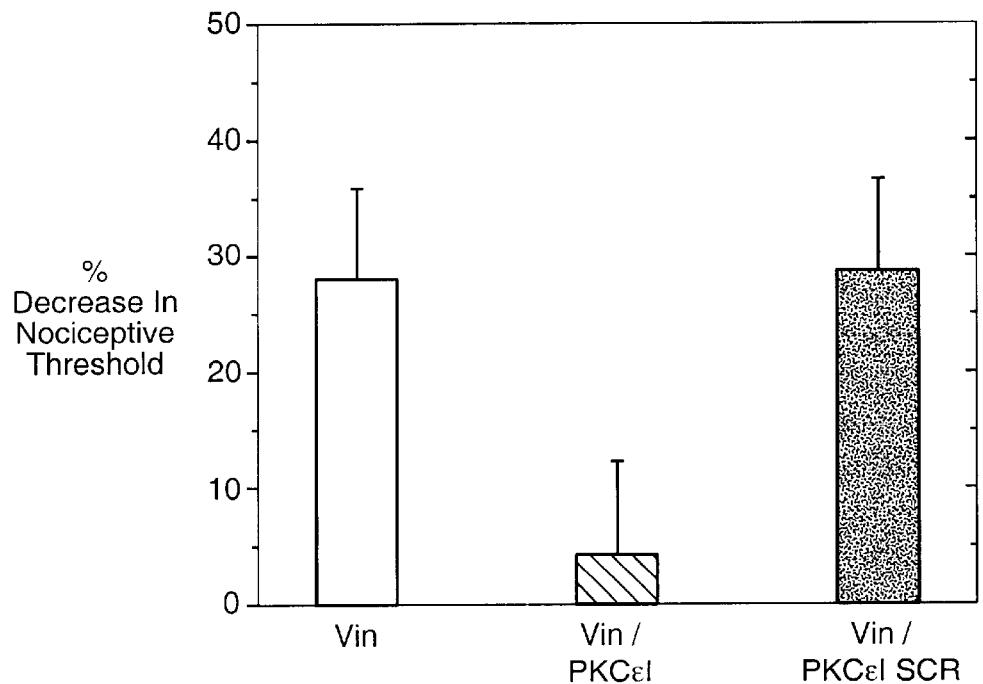
FIG._12A
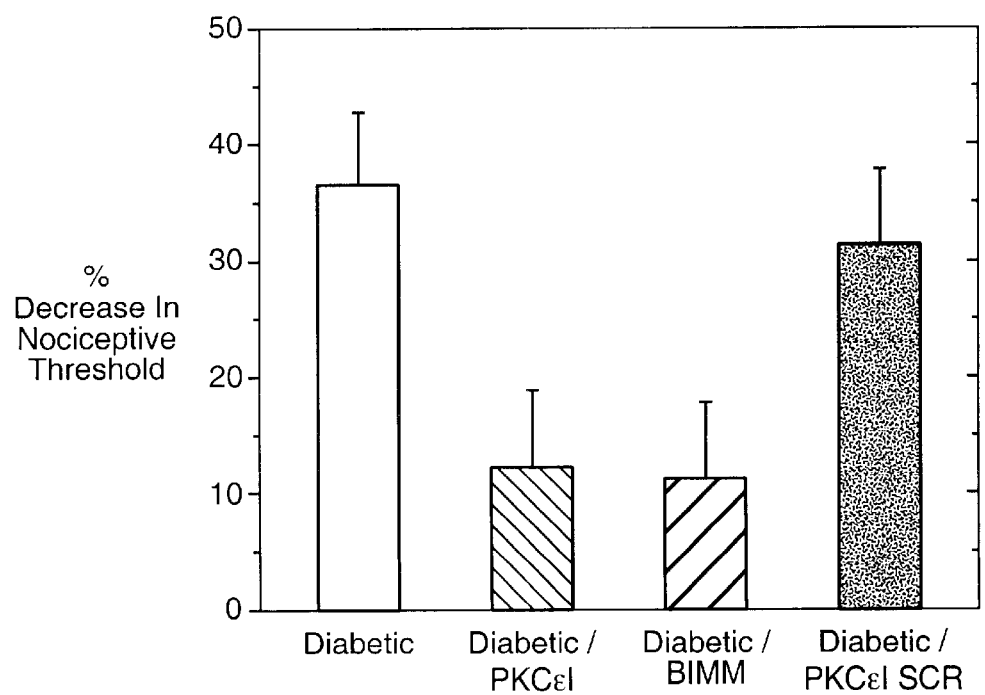
FIG._12B

USE OF INHIBITORS OF PROTEIN KINASE C EPSILON TO TREAT PAIN

CROSS-REFERENCE TO RELATED APPLICATIONS

This application claims the benefit of U.S. Provisional Application No. 60/103,763, filed Oct. 9, 1998. U.S. Provisional Application No. 60/103,763 and U.S. Provisional Application No. 60/091,755 filed Jul. 6, 1998 are incorporated herein by reference.

BACKGROUND

For those who experience it, as well as for their families, communities and employers, pain is more than a minor inconvenience—it is a serious physical, emotional, social and economic burden. Because more than two million people in the United States alone are incapacitated by chronic pain on any given day (T. M. Jessell & D. D. Kelly, Pain and Analgesia in PRINCIPLES OF NEURAL SCIENCE, $3^{rd}$ edition (E. R. Kandel, J. H. Schwartz, T. M. Jessell, ed., 1991)), the number of people and entities bearing these burdens is quite large.

Unfortunately, current treatments for pain are only partially effective, and many also cause debilitating or dangerous side effects. For example, non-steroidal anti-inflammatory drugs ("NSAIDs") such as aspirin, ibuprofen and indomethacin are moderately effective against inflammatory pain but they are also renal toxins, and high doses tend to cause gastrointestinal irritation, ulceration, bleeding and confusion. Patients treated with opioids frequently experience confusion, and long-term opioid use is associated with tolerance and dependence. Local anesthetics such as lidocaine and mixelitine simultaneously inhibit pain and cause loss of normal sensation. Thus, there is a need for safe and effective treatments for pain.

Enhanced understanding of the molecular basis of pain should aid the development of pain medications. Pain is a particularly challenging subject because it is a perception based on signals received from the environment and transmitted and interpreted by the nervous system. Noxious stimuli such as heat and touch cause specialized sensory receptors in the skin to send signals to the central nervous system ("CNS"). This process is called nociception, and the peripheral sensory neurons that mediate it are nociceptors. Depending on the strength of the signal from the nociceptor (s) and the abstraction and elaboration of that signal by the CNS, a person may or may not experience a noxious stimulus as painful.

While pain is not enjoyable, it is crucial—without it, we would be oblivious to many environmental dangers. When our perception of pain is properly calibrated to the intensity of the stimulus, pain serves its intended protective function. However, certain types of tissue damage cause a phenomenon, known as hyperalgesia or pronociception, in which relatively innocuous stimuli are perceived as intensely painful because the person's pain thresholds have been lowered. Both inflammation and nerve damage can induce hyperalgesia. Thus, persons afflicted with inflammatory conditions, such as sunburn, osteoarthritis, colitis, carditis, dermatitis, myositis, neuritis, collagen vascular diseases (which include rheumatoid arthritis and lupus) and the like, often experience enhanced sensations of pain. Similarly, trauma, surgery, amputation, abscess, causalgia, collagen vascular diseases, demyelinating diseases, trigeminal neuralgia, cancer, chronic alcoholism, stroke, thalamic pain syndrome, diabetes, herpes infections, acquired immune deficiency syndrome ("AIDS"), toxins and chemotherapy cause nerve injuries that result in excessive pain. Apparently, the reduced pain thresholds characteristic of hyperalgesia are due to alterations in the way that nociceptors adjacent to the inflammation or damaged nerves respond to noxious stimuli. If the mechanisms by which nociceptors transduce external signals under normal and hyperalgesic conditions were better understood, it might be possible to identify processes unique to hyperalgesia that, when interrupted, could inhibit the lowering of the pain threshold and thereby lessen the amount of pain experienced. Since such a treatment for chronic pain would act at the level of the sensory afferent neurons, it would bypass the problems associated with drugs that act on the CNS. If the treatment incapacitated a transduction pathway specific to nociceptors and/or not involved in mediating other signals, then the potential for treatment-induced side effects would be small. The present invention provides such a method of alleviating pain.

SUMMARY OF THE INVENTION

The present invention is a method of lessening pain comprising administering to a subject in need thereof, an effective amount of an inhibitor of the s isozyme of protein kinase C ("PKCε"). A second aspect of the invention is the use of a PKCε inhibitor to decrease hyperalgesia, preferably without impairing nociception. Inhibitors that are selective for PKCε are preferred, and local administration of the inhibitor is preferred. A third aspect of the invention is a method of identifying compounds that modulate pain comprising selecting a test compound that modulates the activity of PKCε and administering said test compound to a subject to determine whether pain is modulated. A fourth aspect of the invention is a pharmaceutical composition comprising an inhibitor of PKCε and an analgesic agent that is not an inhibitor of PKCε. This invention is well suited to the treatment of subjects having acute or chronic pain caused by neuropathic or inflammatory conditions.

BRIEF DESCRIPTION OF THE DRAWINGS

FIG. 1. Effect of α- and β-adrenergic antagonists, sympathectomy and prostaglandin synthesis inhibitors on epinephrine-induced dose-dependent hyperalgesia in response to mechanical stimuli. Percent decrease in nociceptive thresholds due to injection of 1, 10, 100 and 1000 ng of epinephrine following (A) no treatment (squares), propranolol injection (triangles), phentolamine injection (filled circles) and (B) sham sympathectomy (squares), sympathectomy (bulleyes) and indomethacin injection (inverted triangles).

FIG. 2. Latency and duration of epinephrine-induced hyperalgesia in response to mechanical stimuli. Percent decrease in nociceptive thresholds at indicated number of minutes following 1 μg epinephrine injection.

FIG. 3. Effect of α- and β-adrenergic antagonists on isoproterenol-induced hyperalgesia in response to mechanical stimuli. Percent decrease in nociceptive thresholds due to injection of 1, 10, 100 and 1000 ng of isoproterenol following no treatment (squares), phentolamine injection (diamonds) and propranolol injection (triangles).

FIG. 4(A) Voltage traces from a cultured rat small diameter DRG neuron before and during exposure to 1 μM epinephrine. (B) Effect of 1 μM epinephrine over time on number of action potentials (squares) and latency to first action potential (circles) in another cultured rat small diameter DRG neuron.

FIG. 5. Effect over time of (A) 1 μM epinephrine or (C) isoproterenol on peak tetrodotoxin-resistant sodium current ("TTX-RI$_{Na}$ current"). (B) TTX-RI$_{Na}$ current-voltage plots for no epinephrine (empty circles) and 1 μM epinephrine (filled circles).

FIG. 6. Effect of α- and β-adrenergic antagonists on epinephrine-induced potentiation of TTX-RI$_{Na}$ current. Normalized inward current over time with perfusion of 1 μM epinephrine alone (circles), 1 μM epinephrine and phentolamine (triangles), and 1 μM epinephrine and propranolol (squares).

FIG. 7. Effect of PKA inhibitor on epinephrine-induced potentiation of TTX-RI$_{NA}$ current. Normalized inward current over time with perfusion of 1 μM epinephrine alone (empty circles) or perfusion of 1 μM epinephrine with Rp-cAMPs present in recording pipette (filled circles).

FIG. 8. Effect of PKC inhibitor on epinephrine-induced potentiation of TTX-RI$_{Na}$ current. Normalized inward current over time with perfusion of 1 μM epinephrine alone (empty circles) or perfusion of 1 μM epinephrine with BIM pretreatment (filled circles).

FIG. 9. Mechanical, thermal, and chemical nociception and hyperalgesia in wild-type and PKCε-mutant mice. (A) The responses of wild-type (black bars) and PKCε-mutant (gray bars) mice to mechanical stimuli were examined by measuring paw withdrawal frequencies after von Frey hair ("VFH") stimulation of 4, 6.9 or 14.8 gm intensity. VFH stimulation was preceded by no treatment ("basal"), epinephrine injection, or PGE$_2$ injection. (B) The tolerance of wild-type (black bars) and PKCε-mutant (gray bars) mice to thermal stimuli was determined by measuring length of exposure (in seconds) to a 50 watt radiant heat stimulus prior to paw withdrawal. Heat stimulation was preceded by no treatment ("basal"), epinephrine injection, or PGE$_2$ injection. (C) The ability of intraperitoneal acetic acid injection to induce abdominal contractions ("writhes") was examined in wild-type and PKCε-mutant ("knock-out") mice.

FIG. 10. PKCε expression in rat DRG neurons and skin; inhibition in rats of epinephrine-induced hyperalgesia by a non-selective PKCε inhibitor and a selective PKCε inhibitor. Rat DRG neurons (A) and skin (B and C) were stained with PKCε antibody (A and B) and antibody preabsorbed with antigen (C). Bar=50 μm (A, B and C); Ep=epidermis; De=dermis. Rats received intradermal injections of 100 ng epinephrine ("epi") or 100 ng PGE$_2$ in the wake of injections into the dorsal aspect of the hindpaw of (D) 1 μg bisindolymaleimide I ("BIM"), or (C) sterile water followed either by 1 μg εV1-2 peptide ("VIε1-2,") or 1 μg of a scrambled peptide ("S-VIε1-2"). The change in nociceptive threshold was tested by measuring the response to Ugo Basile stimulation.

FIG. 11. PKCε expression in mouse dorsal root ganglion ("DRG") neurons (A and B) and spinal cord (D and E). Wild-type (A and D) and PKCε-mutant (B and E) mouse tissues were incubated with anti-PKCε antibody. Bar=50 μm (A and B) or 100 μm (D and E). (C) Size frequency histogram of PKCε-expressing and all DRG neurons.

FIG. 12. Effect of PKCε inhibitors on vincristine-induced hyperalgesia (A) or diabetes-induced hyperalgesia (B) in response to mechanical stimuli. Percent decrease in nociceptive thresholds following no treatment (black bars), injection of PKCε inhibitory peptide (diagonal striped bars), injection of a scrambled version of the inhibitory peptide (cross-hatched bars) or injection of bisindolymaleimide I (white bar).

FIG. 13. Effect of PKCε inhibitor on carrageenan-induced hyperalgesia in response to mechanical stimuli. Percent decrease in nociceptive thresholds following exposure to carrageenan alone (white and gray bars—hyperalgesia tested at 3 and 4 hours post carrageenan, respectively), exposure to carrageenan and injection of PKCε inhibitory peptide (black bar), or exposure to carrageenan and injection of a scrambled version of the inhibitory peptide (diagonal striped bar). * indicates significantly different, p<0.0001.

DESCRIPTION OF SPECIFIC EMBODIMENTS

Protein kinase C ("PKC") is a multigene family of phospholipid-dependent, serine-threonine kinases central to many signal transduction pathways. Molecular cloning studies have identified ten members of the PKC family. These family members, called isozymes, are encoded by nine different genes. The ten isozymes are designated as the α, βI, βII, γ, δ, ε, ζ, η, ι/λ and θ isozymes (Y. Nishizuka, *Science* 258, 607–614 (1992); L. A. Selbie, C. Schmitz-Peiffer, Y. Sheng, T. J. Biden, *J. Biol. Chem.* 268, 24296–24302 (1993)). Based on sequence homology and biochemical properties, the PKC gene family has been divided into three groups: (i) the "conventional" PKCs, the α, βI, βII and γ isozymes, are regulated by calcium, diacylglycerol and phorbol esters; (ii) the "novel" PKCs, the δ, ε, θ and η isozymes, are calcium-independent, but diacylglycerol- and phorbol ester-sensitive; and (iii) the "atypical" PKCs, the ζ and ι/λ isozymes, are insensitive to calcium, diacylglycerol and phorbol 12-myristate 13-acetate. In addition, two related phospholipid-dependent kinases, PKCμ and protein kinase D, share sequence homology in their regulatory domains to novel PKCs and may constitute a new subgroup (F.-J. Johannes, J. Prestle, S. Eis, P. Oberhagemann, K. Pfizenmaier, *Biol. Chem.* 269, 6140–6148 (1994); A. M. Valverde, J. Sinnett-Smith, J. Van Lint, E. Rozengurt, *Proc. Natl. Acad. Sci. USA* 91, 8572–8576 (1994)).

It is well established that PKC family proteins play central roles in cell growth and differentiation. PKCs mediate the effects of peptide hormones, growth factors, neurotransmitters and tumor promoters by acting as secondary (downstream, intracellular) messengers for these signaling molecules (Y. Nishizuka, *Science* 233, 305–312 (1986); Y. Takai, K. Kaibuchi, T. Tsuda, M. Hoshijima, *J. Cell. Biochem.* 29, 143–155 (1985)). The identities of the PKC isozymes that transduce particular signals in specific cell types are still being determined. The α, βI, βII, γ, δ, ε and ζ isozymes have been implicated in the differentiation of nonneural cells (E. Berra, et al., *Cell* 74, 555–563 (1993); J. Goodnight, H. Mischak, J. F. Mushinski, *Adv. Cancer Res.* 64, 159–209 (1994); J. R. Gruber, S. Ohno, R. M. Niles, *J. Biol. Chem.* 267, 13356–13360 (1992); D. E. Macfarlane, L. Manzel, *J. Biol. Chem.* 269, 4327–4331 (1994); C. T. Powell et al., *Proc. Natl. Acad. Sci. USA* 89, 147–151 (1992)). Recent studies, showing that the ε isozyme of PKC ("PKCε") is activated by nerve growth factor ("NGF") and mediates NGF-induced neurite outgrowth, were interpreted as indicating a role for PKCε in neuronal differentiation (B. Hundle, et al., *J. Biol. Chem.* 272, 15028–15035 (1997)).

One of the key discoveries underlying the present invention is the demonstration that a specific isozyme of PKC, PKCε, acts in primary afferent nociceptors to mediate certain types of hyperalgesia. In particular, mice that lack functional PKCε protein ("PKCε-mutant mice") show reduced responses to acetic acid injections and decreased epinephrine-induced hyperalgesia in response to mechanical and thermal stimuli. Administration of a peptide that selectively inhibits PKCε also diminishes epinephrine-induced hyperalgesia, carrageenan-induced hyperalgesia and hyperalgesia associated with chemotherapy and diabetes, in response to mechanical stimuli. Because the magnitude of epinephrine-induced hyperalgesia was similar in rats treated with a non-selective PKCε inhibitor and those treated with the selective inhibitor of PKCε, PKCε appears to be the only PKC isozyme mediating epinephrine-induced hyperalgesia. Similarly, because the magnitude of diabetes-associated hyperalgesia was slightly less in rats treated with a non-selective PKCε inhibitor than in those treated with the selective inhibitor of PKCε, PKCε appears to be the major, but perhaps not the only, PKC isozyme mediating diabetes-associated hyperalgesia.

The discovery that PKCε mediates certain types of hyperalgesia was unexpected. Although there was evidence that the PKC family of proteins contributes to diabetic neuropathic hyperalgesia (S. C. Ahlgren, J. D. Levine, *J. Neurophys.* 72, 684–692 (1994)) and to bradykinin-induced activation and sensitization of nociceptors (S. M. McGuirk, A. C. Dolphin, *Neuroscience* 49, 117–28 (1992); L. M. Boland, A. C. Allen, R. Dingledine, *J. Neurosci.* 11, 1140–9 (1991)), the roles of individual PKC isozymes in these processes were unexplored and unpredictable.

A particularly useful aspect of the present invention is the fact that inhibitors of PKCε can reduce hyperalgesia without affecting nociception or compromising other sensory perception. Thus, a person receiving a PKCε inhibitor should have relief from excessive pain stemming from innocuous stimuli while still being able to sense pain in response to intense stimuli. This aspect of the invention is based on experiments using mechanical and thermal stimuli to show that PKCε mediates epinephrine-induced hyperalgesia and carrageenan-induced hyperalgesia but is not involved in nociception (i.e., the basal response). The reduced writhing seen in PKCε-mutant mice injected with acetic acid in comparison to wild-type mice is consistent with PKCε having a role in inflammatory hyperalgesia but not nociception. The theory that acetic acid injection causes inflammation that results in hyperalgesia is supported by data showing that anti-inflammatory drugs (NSAIDs in these cases) inhibit the amount of writhing induced by acetic acid exposure (C. J. Niemegger, J. A. Van Bruggen and P. A. Janssen, *Arzneimittelforschung* 25, 1505–1509 (1975); R. Vinegar, J. F. Truax and J. L. Selph, *Eur. J. Pharmacol.* 37, 23–30 (1976); R. Bjorkman, *Acta Anaesthesiol. Scand. Supp.* 103, 1–44 (1995)). The fact that administration of a selective inhibitor of PKCε nearly eliminates hyperalgesia otherwise caused by carrageenan, a well established inflammatory agent, further solidifies the role of PKCε in mediating inflammatory hyperalgesia.

As described above, the present invention involves the administration of an inhibitor of PKCε to lessen pain, prevent future pain, and/or inhibit heightened sensitivity to a noxious stimulus. Although any molecule that inhibits the PKCS isozyme is sufficient to lessen pain, molecules that selectively inhibit the PKCε isozyme are preferred because, as shown by PKCε-mutant mice, elimination of PKCε does not cause major developmental abnormalities or serious side effects. Since molecules also capable of inhibiting PKC isozymes other than PKCε interfere with the various functions performed by those isozymes, such nonselective inhibitors of PKCε, although they diminish pain, are likely to have many unwanted side effects.

There are many known inhibitors of PKCε that can be used in the instant invention. For instance, U.S. Pat. No. 5,783,405 describes a large number of peptides that inhibit PKC isozymes. Of these, the εV1-1, εV1-2, εV1-3, εV1-4, εV1-5 and εV1-6 peptides are selective for PKCε and are preferred peptide inhibitors. Peptide εV1-2 is a particularly preferred inhibitory peptide. Small molecule inhibitors of PKC are described in U.S. Pat. Nos. 5,141,957, 5,204,370, 5,216,014, 5,270,310, 5,292,737, 5,344,841, 5,360,818, and 5,432,198. These molecules belong to the following classes: N,N'-Bis-(sulfonamido)-2-amino-4-iminonaphthalen-1-ones; N,N'-Bis-(amido)-2-amino-4-iminonaphthalen-1-ones; vicinal-substituted carbocyclics; 1,3-dioxane derivatives; 1,4-Bis-(amino-hydroxyalkylamino)-anthraquinones; furo-coumarinsulfonamides; Bis-(hydroxyalkylamino)-anthraquinones; and N-aminoalkyl amides. Due to their relative ease of administration (for instance, transdermal delivery or ingestion are often feasible for small molecules but not peptides), small molecule inhibitors of PKCε are preferred over peptide inhibitors. The relevant portions of foregoing patents are hereby incorporated by reference.

Additional inhibitors of PKCε can be identified using assays that measure the activation, intracellular translocation, binding to intracellular receptors (e.g. RACKs) or catalytic activity of PKCε. Traditionally, the kinase activity of PKC family members has been assayed using at least partially purified PKC in a reconstituted phospholipid environment with radioactive ATP as the phosphate donor and a histone protein or a short peptide as the substrate (T. Kitano, M. Go, U. Kikkawa, Y. Nishizuka, *Meth. Enzymol.* 124, 349–352 (1986); R. O. Messing, P. J. Peterson, C. J. Henrich, *J. Biol. Chem.* 266, 23428–23432 (1991)). Recent improvements include a rapid, highly sensitive chemiluminescent assay that measures protein kinase activity at physiological concentrations and can be automated and/or used in high-throughput screening (C. Lehel, S. Daniel-Issakani, M. Brasseur, B. Strulovici, *Anal. Biochem.* 244, 340–346 (1997)) and an assay using PKC in isolated membranes and a selective peptide substrate that is derived from the MARCKS protein (B. R. Chakravarthy, A Bussey, J. F. Whitfield, M. Sikorska, R. E. Williams, J. P. Durkin, *Anal. Biochem.* 196, 144–150 (1991)). Inhibitors that affect the intracellular translocation of PKCε can be identified by assays in which the intracellular localization of PKCε is determined by fractionation (R. O. Messing, P. J. Peterson, C. J. Henrich, *J. Biol. Chem.* 266, 23428–23432 (1991)) or immunohistochemistry (U.S. Pat. No. 5,783,405; U.S. patent application Ser. No. 08/686,796 now U.S. Pat. No. 6,255,057, now U.S. Pat No 6,255,057). To identify an inhibitor of PKCε, the assays should be performed with PKCε. The selectivity of such PKCε inhibitors can be determined by comparing the effect of the inhibitor on PKCε with its effect on other PKC isozymes. The relevant portions of foregoing patents and publications are hereby incorporated by reference.

Because PKCε is an intracellular protein, preferred embodiments of the invention involve pharmaceutically acceptable inhibitor formulations capable of permeating the plasma membrane. Small, apolar molecules are often membrane permeable. The membrane permeability of other molecules can be enhanced by a variety of methods known to those of skill in the art, including dissolving them in hypotonic solutions, coupling them to transport proteins, and packaging them in micelles.

PKCε inhibitors can be administered hourly, several times per day, daily or as often as the person experiencing the pain or that person's physician sees fit. Preferably, the administration interval will be in the range of 8 to 24 hours. The severity of the patient's pain can be taken into account when determining appropriate intervals for PKCε inhibitor treatments. PKCε inhibitor treatments can continue over the course of several days, one month, several months, one year, several years or the duration of the patient's lifetime.

Alternatively, PKCε inhibitors can be administered on a one-time only basis provided that the pain is expected to be transient and it does not reappear. PKCε inhibitors should be administered at levels sufficient to reduce pain in the body of the patient. The skilled artisan will appreciate that increasing doses of PKCε inhibitors should be administered until the patient experiences pain reduction, and larger doses fail to effect greater pain amelioration. Administration could be set up such that the patient can control future dosages of PKCε inhibitor according to the amount of pain they experience.

Inhibitor dosage will vary according to many parameters, including the nature of the inhibitor and the mode of administration. For the εPKC-v1 peptide, a 150 μg/ml intracellular concentration inhibited PKCε translocation and downstream effects of PKCε activation (U.S. Pat. No. 5,783,405). Daily dosages in the range of 1 μg/kg–100 mg/kg of body weight, preferably 1 μg/kg–1 mg/kg and most preferably 10 μg/kg–1 mg/kg are contemplated for PKC inhibitors that are N,N'-Bis-(sulfonamido)-2-amino-4-iminonaphthalen- 1-ones or N,N'-Bis-(amido)-2-amino-4-iminonaphthalen-1-ones. Daily dosages in the range of 1 μg/kg–100 mg/kg of body weight, preferably 1 μg/kg–40 mg/kg and most preferably 10 μg/kg–20 mg/kg are contemplated for PKC inhibitors that are vicinal-substituted carbocyclics. Daily dosages in the range of 5–400 mg/kg of body weight, preferably 10–200 mg/kg and most preferably 10–50 mg/kg are contemplated for PKC inhibitors that are 1,4-Bis-(amino-hydroxyalkylamino)-anthraquinones, Bis-(hydroxyalkylamino)-anthraquinones, or N-aminoalkyl amides. Daily dosages in the range of 0.1–40 mg/kg of body weight, preferably 1–20 mg/kg, are contemplated for PKC inhibitors that are 1,3-dioxane derivatives. Daily dosages in the range of 1–100 mg/kg of body weight are contemplated for PKC inhibitors that are furo-coumarinsulfonamides.

PKCε inhibitors can be locally administered near the site of inflammation or peripheral nerve damage. Such local administration can be topical or by intradermal or subcutaneous injection. Systemic administration of a PKCε inhibitor represents another embodiment of the invention. Oral and intravenous injection are preferred types of systemic administration. Since PKCε appears to modulate pain at the level of the peripheral nociceptors and may perform other functions in the brain, local administration of PKCε inhibitors is more preferable than systemic administration because local administration should effectively treat pain in the vicinity with minimal deleterious effects on PKCε activity in distant locations. The methods of this invention are useful for treating mammals in general and humans in particular.

A preferred embodiment of the present invention is the administration of a pharmaceutically acceptable formulation of an inhibitor of PKCε. A "pharmaceutically acceptable formulation" comprises one that is suitable for administering the PKCε inhibitor in a manner that gives the desired results and does not also produce adverse side effects sufficient to convince a physician that the potential harm to a patient is greater than the potential benefit to that patient. The basic ingredient for an injectable formulation is a water vehicle. The water used will be of a purity meeting USP standards for sterile water for injection. Aqueous vehicles that are useful include sodium chloride (NaCl) solution, Ringer's solution, NaCl/dextrose solution, and the like. Water-miscible vehicles are also useful to effect full solubility of the PKCε inhibitor. Antimicrobial agents, buffers and antioxidants are useful, depending on the need.

In preparing PKCε inhibitor compositions for this invention, one can follow the standard recommendations of well known pharmaceutical sources such as REMINGTON: THE SCIENCE AND PRACTICE OF PHARMACY, 19$^{th}$ ed., (Mack Publishing, 1995). In general, the pharmaceutical composition of this invention is powder- or aqueous-based with added excipients that aid in the solubility of the PKCε inhibitor, the isotonicity of the composition, the chemical stability and the deterrence of microorganism growth. For oral administration, it is preferable to include substances that protect the PKCε inhibitor from degradation by digestive agents.

A preferred embodiment of the invention is the treatment of a patient having inflammatory pain. Such inflammatory pain may be acute or chronic and can be due to any number of conditions characterized by inflammation including, without limitation, sunburn, rheumatoid arthritis, osteoarthritis, colitis, carditis, dermatitis, myositis, neuritis and collagen vascular diseases. This embodiment of the invention is based on experiments showing that administration of a PKCε inhibitor significantly diminishes both acute and chronic hyperalgesia resulting from exposure to the inflammatory agent carrageenan. The fact that PKCε inhibitors effectively reduce chronic hyperalgesia when administered long after the inflammatory agent (carrageenan in these experiments) indicates that persons who have long suffered pain associated with inflammatory diseases such as those listed above should experience at least partial pain relief following administration of an inhibitor of PKCε. In addition, administration of an PKCε inhibitor to a subject immediately prior to, during or after an inflammatory event can ameliorate both the acute pain and the chronic hyperalgesia that the subject would otherwise experience.

Another preferred embodiment of the invention is the treatment of a patient having neuropathic pain. Such patients can have a neuropathy classified as a radiculopathy, mononeuropathy, mononeuropathy multiplex, polyneuropathy or plexopathy. Diseases in these classes can be caused by a variety of nerve-damaging conditions or procedures, including, without limitation, trauma, stroke, demyelinating diseases, abscess, surgery, amputation, inflammatory diseases of the nerves, causalgia, diabetes, collagen vascular diseases, trigeminal neuralgia, rheumatoid arthritis, toxins, cancer (which can cause direct or remote (e.g. paraneoplastic) nerve damage), chronic alcoholism, herpes infection, AIDS, and chemotherapy. Nerve damage causing hyperalgesia can be in peripheral or CNS nerves. This embodiment of the invention is based on experiments showing that administration of a PKCε inhibitor significantly diminishes hyperalgesia due to diabetes, chemotherapy or traumatic nerve injury.

It is believed that inhibitors of PKCε lessen pain by interfering with PKCε function in sensory afferent neurons (also known as nociceptors or primary afferent neurons). These neurons, a subset of small- and medium-diameter dorsal root ganglion neurons ("DRG neurons"), extend from the dermis, where their peripheral terminals are located, to the superficial laminae of the dorsal horn, where they synapse with CNS neurons. In sensory afferent neurons, PKCε is believed to be a secondary messenger transducing a response initiated by a noxious stimulus or a hyperalgesia-inducing agent.

Some of the observations underlying the present invention were made in experiments in which hyperalgesia was induced by intradermal injection of epinephrine into the hindpaw of a mouse or rat. Epinephrine-induced hyperalgesia is a model system for the study of naturally occurring hyperalgesia, and the clinical relevance of this system is supported by the fact that local administration of epinephrine exacerbates symptoms in patients with neuropathic pain (B. Choi, M. C. Rowbotham, *Pain* 69, 55–63 (1997)) and that epinephrine causes anginal pain in the absence of apparent ischemia (B. Eriksson et al., *Am. J. Cardiol.* 75, 241–245 (1995)). Epinephrine causes dose-dependent mechanical and thermal hyperalgesia in sensory nerve terminals in the skin by binding to 0-adrenergic receptors on these nerve terminals. The β-adrenergic receptors bound by epinephrine in turn activate two independent second messenger pathways, the PKC pathway and the cyclic AMP ("cAMP")/protein kinase A ("PKA") pathway. Although epinephrine-induced hyperalgesia is not mediated by prostaglandins, both epinephrine and prostaglandin $E_2$ ("$PGE_2$"), enhance the tetrodotoxin-resistant sodium current ($TTX-RI_{Na}$), which is important in inflammatory mediator-induced hyperalgesia and nociceptor sensitization. Since PKC inhibitors reduce the effect of epinephrine on that current, $TTX-RI_{Na}$ can be a target of PKC, as well as of PKA.

The direct action of epinephrine on primary sensory afferent neurons is in contrast to other hyperalgesia-inducing agents which indirectly sensitize these neurons. For instance, bradykinin and norepinephrine affect nociceptors by causing intermediary cells to release prostaglandins that act on nociceptors and by causing sympathetic neurons to send signals to nociceptors (N. Y. Andreev, N. Dimitrieva, M. Koltzenburg, S. B. McMahon, *Pain* 63, 109–115 (1995); S. H. Ferreira, et al., *Brit. J. Pharmacol.* 121, 883–888 (1997); Y. O. Taiwo, P. H. Heller, J. D. Levine, *Neuroscience* 39, 523–531 (1990)). The fact that neither inhibition of prostaglandin synthesis nor hindpaw sympathectomy (elimination of sympathetic innervation of the hindpaw) had any effect on the ability of epinephrine to induce hyperalgesia shows that epinephrine's sole mode of action is direct. Epinephrine's direct effects on the primary afferent nociceptor provide further evidence that it is a good model to explore the contribution of the PKC isozyme(s) involved in nociceptive signaling.

Another aspect of the invention is a method of identifying a compound that modulates pain, by selecting, as a test compound, a compound that modulates the activity of PKCε, and administering said test compound to a subject to determine whether pain is modulated. Preferably, the compound will inhibit the activity of PKCε, and the subject will be an animal commonly used in pain research and/or development. The ability of a test compound to inhibit, enhance or modulate the activity of PKCε may be determined with suitable assays measuring PKCε's function. For example, responses such as its activity, e.g., enzymatic activity, or PKCε's ability to bind its ligand, adapter molecule or substrate may be determined in in vitro assays. Cellular assays can be developed to monitor a modulation of second messenger production, changes in cellular metabolism, or effects on enzymatic activity. These assays may be performed using conventional techniques developed for these purposes. Finally, the ability of a test compound to inhibit, enhance or modulate the function of PKCε will be measured in suitable animal models in vivo.

Preferred embodiments of the present invention include a composition combining an inhibitor of PKCε with one or more additional pain-reducing agents and a method of administering such a composition. An individual pain medication often provides only partially effective pain alleviation because it interferes with just one pain-transducing pathway out of many. For instance, experiments presented herein show that PKCε and PKA are both secondary messengers of epinephrine-induced hyperalgesia. The pain associated with this type of hyperalgesia can be more effectively addressed by inhibiting both PKCε and PKA than by inhibiting PKCε alone. Alternatively, PKCε inhibitors can be administered in combination with a pain-reducing (analgesic) agent that acts at a different point in the pain perception process. A PKCε inhibitor can minimize pain by altering the responses of nociceptors to noxious stimuli. One class of analgesics, such as NSAIDs, down-regulates the chemical messengers of the stimuli that are detected by the nociceptors and another class of drugs, such as opioids, alters the processing of nociceptive information in the CNS. Other analgesics are local anesthetics, anticonvulsants, and antidepressants. Administering one or more classes of drug in addition to PKCε inhibitors can provide more effective amelioration of pain. NSAIDs are preferred components of the composition of the invention. Preferred NSAIDs are aspirin, acetaminophen, ibuprofen, and indomethacin.

The term "lessening pain" as used herein comprises a process by which the level of pain a subject perceives is reduced relative to the level of pain the subject would have perceived were it not for the intervention. Where the subject is a person, the level of pain the person perceives can be assessed by asking him or her to describe the pain or compare it to other painful experiences. Alternatively, pain levels can be calibrated by measuring the subject's physical responses to the pain, such as the release of stress-related factors or the activity of pain-transducing nerves in the peripheral nervous system or the CNS. One can also calibrate pain levels by measuring the amount of a well characterized analgesic required for a person to report that no pain is present or for a subject to stop exhibiting symptoms of pain. Lessening pain can result from increasing the threshold at which a subject experiences a given stimulus as painful. It can result from inhibiting hyperalgesia, the heightened sensitivity to a noxious stimulus, and such inhibition can occur without impairing nociception, the subject's normal sensitivity to a noxious stimulus.

"A subject in need thereof" comprises an animal or person, preferably a person, expected to experience pain in the near future. Such animal or person may have a ongoing condition that is causing pain currently and is likely to continue to cause pain, or the animal or person has been, is or will be enduring a procedure or event that usually has painful consequences. Chronic painful conditions such as diabetic neuropathic hyperalgesia and collagen vascular diseases are examples of the first type; dental work, particularly in an area of inflammation or nerve damage, and toxin exposure (including exposure to chemotherapeutic agents) are examples of the latter type.

"An effective amount" comprises an amount that results in the lessening of pain. Such effective amount will vary from subject to subject depending on the subject's normal sensitivity to pain, its height, weight, age, and health, the source of the pain, the mode of administering the inhibitor of PKCε, the particular inhibitor administered, and other factors. As a result, it is advisable to empirically determine an effective amount for a particular subject under a particular set of circumstances.

"An inhibitor of the ε isozyme of protein kinase C (PKCε)" comprises a molecule or group of molecules that interferes with: (1) the expression, modification, regulation or activation of PKCε, (2) one or more of the normal functions of PKCε, or (3) the expression, modification, regulation or activation of a molecule acting downstream of PKCε in a PKCε-dependent pathway. The normal functions of PKCε, many of which are activation-dependent, include the phosphorylation of substrates (i.e., the catalytic activity of PKCε), autophosphorylation, movement from one intracellular location to another upon activation (i.e., intracellular translocation), and binding to or release from one or more proteins that anchor PKCε in a given location. An inhibitor of PKCε can also inhibit other isozymes of PKC. However, a selective inhibitor of PKCε significantly inhibits one or more normal functions of PKCε at a concentration at which the other isozymes of PKC are not significantly inhibited. An inhibitor "acts directly on PKCε" when the inhibitor binds to PKCε via electrostatic or chemical interactions. Such interactions may or may not be mediated by other molecules. An inhibitor acts "indirectly on PKCε" when its most immediate effect is on a molecule, other than PKCε, that influences the expression, activation or functioning of PKCε or the downstream effects of PKCε.

A compound or molecule "modulates the activity of PKCε" if it affects (1) one or more of the normal functions of PKCε, or (2) the expression, modification, regulation, activation or degradation of PKCε or a molecule acting upstream of PKCε in a regulatory or enzymatic pathway. The normal functions of PKCε, many of which are activation-dependent, include the phosphorylation of substrates (i.e., the catalytic activity of PKCε), autophosphorylation, movement from one intracellular location to another upon activation (i.e., intracellular translocation), and binding to or release from one or more proteins that anchor PKCε in a given location.

The difference between "acute" and "chronic" pain is one of timing: acute pain is experienced soon (preferably within about 48 hours, more preferably within about 24 hours, most preferably within about 12 hours) after the occurrence of the event (such as inflammation or nerve injury) that led to such pain. By contrast, there is a significant time lag between the experience of chronic pain and the occurrence of the event that led to such pain. Such time lag is at least about 48 hours after such event, preferably at least about 96 hours after such event, more preferably at least about one week after such event.

"Neuropathic pain" comprises pain arising from conditions or events that result in nerve damage. "Neuropathy" comprises a disease process resulting in damage to nerves. "Causalgia" denotes a state of chronic pain following nerve injury or a condition or event, such are cardiac infarction, that causes referred pain. "Allodynia" comprises a condition in which a person experiences pain in response to a normally nonpainful stimulus, such as a gentle touch. An "analgesic agent" comprises a molecule or combination of molecules that causes a reduction in pain. An analgesic agent employs a mechanism of action other than inhibition of PKCε when its mechanism of action does not involve direct (via electrostatic or chemical interactions) binding to and reduction in the function of PKCε or any intracellular molecule in the PKCε pathway.

The specific items mentioned in the foregoing definitions represent preferred embodiments of the present invention.

EXAMPLES

Example 1

Epinephrine-Induced Hyperalgesia is Prostaglandin-Independent and is Mediated by β-Adrenergic Receptors, PKC, Protein Kinase A and μ Opioid Receptors As shown in FIG. 1A, intradermal injections of 1 ng to 1 μg epinephrine into the dorsal surface of the hindpaw of a rat produced a dose-dependent decrease (F=90.7, p<0.01) in the threshold at which the rat withdrew the paw in response to the application of a linearly increasing mechanical force by the Ugo Basile Analgesimeter (Stoelting, Chicago, Ill.). The onset latency of this epinephrine-induced hyperalgesia was brief—it was significant 2 minutes after 1 μg epinephrine injection, reached a peak effect by 5 minutes (FIG. 2A) and lasted approximately 2 hours (FIG. 2B).

Since epinephrine has affinity for both α- and β-adrenergic receptors ("α-AR" and "β-AR", respectively), the contribution of α-AR to epinephrine-induced hyperalgesia was tested using phentolamine, an α-AR antagonist. Earlier studies showed that a similar dose of phentolamine had no effect on basal paw threshold in the normal rat but significantly reversed formalin-induced hyperalgesia and inhibited the ability of rolipram, an inhibitor of type IV phosphodiesterase, to prolong $PGE_2$-induced hyperalgesia (J. D. Levine et al., Nature 323, 158–160 (1986); A. K. Ouseph et al., Neurosci. 64, 769–776 (1995)). However, phentolamine did not significantly affect epinephrine-induced hyperalgesia (FIG. 1A), demonstrating that α-AR does not mediate the hyperalgesic effects of epinephrine.

To examine the role of β-AR in epinephrine-induced hyperalgesia, propranolol, a β-AR antagonist, and isoproterenol, a selective β-AR agonist, were administered by intradermal injection. Isoproterenol produced dose-dependent hyperalgesia in the absence of epinephrine (FIG. 3). Propranolol significantly attenuated both the hyperalgesia caused by isoproterenol and that due to epinephrine (FIGS. 3 and 1A, respectively). Thus, epinephrine produces hyperalgesia by activating β-AR.

Bradykinin and norepinephrine are known to cause hyperalgesia indirectly, by triggering other cells to produce prostaglandins that have a sensitizing effect on primary afferent neurons and by stimulating sympathetic neurons that influence nociceptors (J. D. Levine et al., Nature 323, 158–160 (1986); Y. O. Taiwo, P. H. Heller, J. D. Levine, Neurosci. 39, 523–531 (1990)). To test whether epinephrine also causes hyperalgesia indirectly, prostaglandin synthesis was inhibited by continuous treatment with 4 mg/kg of indomethacin (n=8) and the contribution of sympathetic neurons was eliminated by sympathectomy (n=8). Neither indomethacin treatment nor sympathectomy had any effect on the ability of epinephrine to induce hyperalgesia (FIG. 1B). This suggests that epinephrine acts directly on nociceptive DRG neurons.

The roles of PKC, protein kinase A ("PKA") and the μ-opioid receptor in mediating epinephrine-induced hyperalgesia were assessed by measuring the effects of: Rp-adenosine 3', 5'-cyclic monophosphate ("Rp-cAMPs") and WIPTIDE, both inhibitors of PKA; SQ22536, an inhibitor of adenylyl cyclase, an enzyme activated by PKA; bisindolymaleimide ("BIM"), a nonselective inhibitor of PKC isozymes; and [D-Ala$^2$,N-Me-Phe$^4$,Gly$^5$-ol]-enkephalin ("DAMGO"), μ-opioid receptor agonist. The dose for each inhibitor was 1 μg, except for WIPTIDE, which was administered in a 100 ng dose. DAMGO was co-injected with epinephrine whereas the other inhibitors were applied 15 minutes prior to epinephrine injection. As shown in Table 1, all of these inhibitors significantly attenuated epinephrine-induced hyperalgesia, showing that epinephrine-mediated hyperalgesia is mediated by the PKC and PKA pathways and by μ-opioid receptors. The same dose of BIM had no effect on $PGE_2$-induced hyperalgesia but significantly attenuated isoproterenol-induced hyperalgesia. In contrast, the same dose of WIPTIDE also significantly attenuated $PGE_2$-induced hyperalgesia and almost completely abolished isoproterenol-induced hyperalgesia. This shows a role for PKA in both prostaglandin- and β-AR-mediated hyperalgesia and a role for PKC in the latter only.

TABLE 1

Percentage decrease in nociceptive threshold in response to epinephrine, PGE$_2$ or isoproterenol (each 100 ng) and effects of DAMGO, SQ22536, BIM, Rp-cAMPs (all 1 μg) or WIPTIDE (0.1 μg). A large numeric value means more hyperalgesia.

|  | Epinephrine | PGE$_2$[§] | Isoproterenol |
| --- | --- | --- | --- |
| Alone | 29.6 ± 2.1 (n = 24) | 33.6 ± 1.9 (n = 20) | 25.8 ± 0.9 (n = 16) |
| DAMGO | 11.5 ± 3.1* (n = 6) | 11.1 ± 4.0** (n = 8) |  |
| SQ22536 | 9.5 ± 2.4* (n = 8) | 10.0 ± 2.9** (n = 11) |  |
| BIM | 4.6 ± 2.1* (n = 6) | 33.4 ± 4.1 (n = 6) | 7.1 ± 2.4*† (n = 12) |
| Rp-cAMPs | 13.9 ± 4.6* (n = 6) | 3.1 ± 5.2** (n = 6) |  |
| WIPTIDE | 10.9 ± 3.6* (n = 6) | 9.4 ± 3.1** (n = 6) | 1 ± 2.8*† (n = 6) |

*Significantly different from epinephrine alone (P<0.01).
*†Significantly different from isoproterenol alone (P<0.01).
**Significantly different from PGE$_2$ alone (P<0.01).
[§]PGE$_2$ data are from (S. G. Khasar et al., Neurosci. 64, 1161–1165 (1995)) or (Y.O. Taiwo and J. D. Levine, Neurosci, 44, 131–135 (1991)), except for BIM and WIPTIDE.

Example 2

Epinephrine Causes Epinephrine-Induced Hyperalgesia by Acting Directly on Primary Afferent Nociceptors To test whether the epinephrine-induced hyperalgesia measured using behavioral models is due to the direct action of epinephrine on primary afferent nociceptors, whole-cell patch-clamp experiments were performed on dissociated, small diameter DRG neurons within 12–24 hours of plating. These neurons have been previously shown to serve as a model for peripheral nociceptor terminals (P. I. Baccaglini and P. G. Hogan, Proc. Natl. Acad. Sci. USA 80, 594–598 (1983); S. Pitchford and J. D. Levine, Neurosci. Let. 132, 105–108 (1991); S. England et al., J. Physiol. London 495, 429–440 (1996); M. S. Gold et al., Neurosci. 71, 265–275 (1996)).

Current-clamp recordings were performed using the perforated-patch whole-cell technique. The number of action potentials generated during a 750 ms ramp-and-plateau depolarizing current injection, as well as the latency to the first spike, were used as a measure of excitability. After 5–10 minutes of baseline recordings, epinephrine (1 μM) was added to the bath. FIG. 4A shows voltage traces from a typical neuron before and during exposure to 1 μM epinephrine, while FIG. 4B shows the time course of changes in the number of action potentials and the latency to the first action potential for another cell. For 11 neurons treated with 1 μM epinephrine, the average number of action potentials generated in response to the current ramp-and-plateau was 1.7±0.2 before the addition of epinephrine and 5.3±0.9 five minutes or more after the start of drug perfusion (p<0.005). When no epinephrine was present, the mean latency from the start of current injection to the peak of the first spike was 278±42 ms; following epinephrine perfusion, the mean latency became 189±21 ms (n=11, p<0.05). Nine (81%) of the 11 neurons tested showed an increase in spike number and 5 (45%) of these neurons also showed a decrease in spike latency of at least 50 ms. Mean resting potentials were unaffected by epinephrine.

The fact that the addition of 10 μM of propranolol 30 seconds prior to and with 1 μM epinephrine abolished the increase in spike number (1.2±0.1 before and 1.3±0.2 after epinephrine addition, n=7, p<0.05) and decrease in first-spike latency (235±9 ms before and 233±10 ms after epinephrine addition, n=7, p<0.05) usually caused by epinephrine demonstrates that, like in the behavioral studies, epinephrine acts on primary afferent neurons by activating β-AR.

Since hyperalgesic agents that sensitize nociceptors in vitro have been shown to increase TTX-RI$_{Na}$ (S. England et al., J. Physiol. London 495, 429–440 (1996); M. S. Gold et al., Proc. Natl. Acad. Sci. USA 93, 1108–1112 (1996)), epinephrine's effect on TTX-RI$_{Na}$ was examined. As shown in FIG. 5, 1 μM epinephrine caused a marked potentiation of TTX-RI$_{NA}$ shifting the current-voltage plots for activation by approximately 10 mV in the hyperpolarized direction (FIG. 5B). This dose of epinephrine caused an increase in TTX-RI$_{Na}$ in 14 out of 21 (67%) neurons. Since isoproterenol application produced similar results as epinephrine (FIG. 5C) and 2 μM propranolol eliminated this potentiation but 5 μM phentolamine did not, epinephrine's effects on TTX-RI$_{Na}$ are mediated by β-AR and not α-AR.

The roles of PKC and PKA in mediating epinephrine-induced potentiation of TIX-RI$_{Na}$ were tested by the addition of 100 μM Rp-cAMPs or 100 M μM. Rp-cAMPs abolished and BIM significantly decreased (n=11, p<0.01) epinephrine-induced potentiation TTX-RI$_{NA}$ (FIGS. 7 and 8), thus demonstrating involvement of the PKA and PKC pathways. PKC inhibition by BIM decreased the number of neurons (5 out of 11 v. 8 out of 11) responsive to epinephrine and the magnitude of their responses (mean peak current increase of 32% v. 49%).

Thus, the epinephrine-induced hyperalgesia displayed by animals is due to epinephrine's stimulation of β-adrenergic receptors and PKC and PKA pathways in primary afferent nociceptors.

Example 3

Hyperalgesic Responses to Mechanical and Thermal Stimuli as well as Acetic Acid Injection are Significantly Diminished in the Absence of PKCε

One of the most powerful methods for testing the role of a protein in a process is to generate mutant animals that lack the protein and to compare the process in mutant animals with that in their wild-type counterparts. To examine whether PKCε plays a role in pain signaling, homozygous PKCε-mutant mice were generated by homologous recombination, production of chimeric mice and subsequent breeding. The construction of these mice is described in detail in the U.S. Provisional Patent Application entitled "PKCε as Modulator of Anxiety" and filed on Jul. 6, 1998, which is hereby incorporated by reference. PKCε-mutant mice are viable and cannot be distinguished from wild-type littermates in the normal cage environment. Moreover, hematoxylin and eosin staining of the brain, spinal cord and DRG neurons showed no anatomical abnormalities.

Mechanical, thermal and chemical nociception were evaluated in wild-type and PKCε-mutant mice. For both wild-type (n=8) and PKCε-mutant (n=8) mice, the basal mechanical nociceptive threshold was measured as the frequency at which mice withdrew their paws after being poked in the hindpaw with a von Frey Hair ("VFH"; Stoelting Co.) applying a force of 4, 6.9 or 14.8 grams. As shown in FIG. 9A, the percent-withdrawal response after VFH stimulation was similar in wild-type and mutant mice. When 100 ng of epinephrine or prostaglandin $E_2$ ("$PGE_2$") was administered by intraplantar injection prior to VFH stimulation, the percent-withdrawal response to a particular intensity of VFH stimulus dramatically increased in wild-type mice, indicating that the injected compounds lower nociceptive thresholds (E. Kinnman, J. D. Levine, Neuroscience 64, 751–767 (1995)). While mutant mice and wild-type mice demonstrated similar percent-withdrawal responses to VFH stimulation after exposure to $PGE_2$, the percent-withdrawal response following epinephrine injection was significantly lower ($p=0.0013$ for 4 gram VHF; $p=0.0692$ for 6.9 gram VHF; and $p=0.0023$ for 14.8 gram VHF PKCε-mutant mice than in wild-type mice (FIG. 9A).

When thermal nociceptive thresholds were determined by the Hargreave thermal nociceptive test (K. O. Aley, D. B. Reichling, J. D. Levine, Neuroscience 73, 259–265 (1996)), wild-type (n=8) and mutant (n=8) mice demonstrated similar basal thresholds and similar responses to $PGE_2$, but PKCε-mutant animals displayed significantly reduced ($p=0.0006$) epinephrine-induced thermal hyperalgesia compared to their wild-type littermates (FIG. 9B).

Chemically induced hyperalgesia in wild-type (n=4) and mutant (n=4) mice was determined by the acetic acid writhing test (S. J. Ward, A. E. Takemori, J. Pharmacol. Exp. Ther. 224, 525–530 (1983)). As demonstrated in FIG. 9C, PKCε-mutant mice have significantly lower ($p=0.0124$) nociceptive thresholds than wild-type animals.

The presence of normal $PGE_2$-mediated responses in PKCε-mutant mice is consistent with data indicating that $PGE_2$ hyperalgesia and sensitization is not dependent on PKC, but instead is dependent on PKA (G. R. Lewin, A. M. Ritter, L. M. Mendell, J. Neurosci. 13, 2136–2148 (1993)). These studies suggest that a defect in PKCε-mediated signal transduction accounts for reduced epinephrine-mediated hyperalgesia in PKCε-mutant mice. The lower score in the acetic acid writhing test in PKCε-mutant mice also suggests that PKCε contributes to inflammatory pain. The findings that PKCε does not contribute to baseline nociceptive thresholds and that the mutant mice act and appear normal indicate that inhibitors of PKCε can ameliorate pain without causing serious systemic side effects or interfering with normal nociceptive responses.

Example 4

Administration of a Selective Inhibitor of PKCε Lessens Hyperalgesia in Response to a Mechanical Stimulus To confirm that the hyperalgesic responses of PKCε-mutant mice reported in Example 3 are due to PKCε's role in these processes rather than a possible requirement for PKCε during development of the nervous system, the nociceptive and hyperalgesic responses of wild-type adult (200–250 gm) Sprague-Dawley rats obtained from Bantin-Kingman (Fremont Calif.) were examined immediately following treatment with a selective inhibitor of PKCε, the εV1-2 peptide. This peptide selectively inhibits the ε isozyme of PKC by interfering with its activation-induced translocation—in the presence of εV1-2, the binding of PKCε to β'COP, its anchoring protein, is impaired (J. A. Johnson, M. O. Gray, C.-H. Chen, D. Mochly-Rosen, J. Biol. Chem. 271, 24962–24966 (1996); M. Csukai, C.-H. Cehn, M. A. De Matteis, D. Mochly-Rosen, J. Biol. Chem. 272, 29200–29206 (1997); B. Hundle, et al., J. Biol. Chem. 272, 15028–15035 (1997)).

For mechanical nociceptive testing, the nociceptive flexion reflex was quantified 2,0 using an Ugo Basile analgesymeter that applies a constantly increasing force measured in grams (Stoelting, Chicago, Ill.; K. O. Aley, J. D. Levine, J. Neurosci. 17, 8018–23 (1997)). The mean basal mechanical threshold for rats used in these experiments was 105.3+/−2.8 grams. The effects of hyperalgesia-inducing agents epinephrine (100 ng) and $PGE_2$ (100 ng) on mechanical nociceptive thresholds were determined by measuring paw withdrawal frequencies at 15, 20, and 25 minutes after administration of the hyperalgesic agent and then calculating the mean of these three readings. As shown in FIG. 10E, the mechanical nociceptive thresholds of rats (n=8) that received footpad injections of sterile water (to create a hypotonic environment) and 1 μg of a scrambled version of the εV1-2 peptide prior to epinephrine treatment were very similar to those of rats (n=8) treated only with epinephrine; both groups showed an approximately 25–30% threshold reduction. In contrast, rats (n=8) that received footpad injections of sterile water (to create a hypotonic environment) and 1 μg of the εV1-2 peptide prior to epinephrine treatment, exhibited significantly less epinephrine-induced threshold reduction (FIG. 10E). As expected, rats that received εV1-2 and $PGE_2$ (n=10) showed threshold reductions that were indistinguishable from those of rats receiving just $PGE_2$ (n=10). These results demonstrate that inhibition of PKCε in adult neurons reduces epinephrine-mediated hyperalgesia.

Example 5

PKCε Is The Only PKC Isozyme Involved In Epinephrine-Induced Hyperalgesia

To assess the contribution of PKC isozymes other than PKCε to epinephrine-induced hyperalgesia, we co-injected epinephrine with a PKC inhibitor that is not isozyme-selective, bisindolymaleimide I ("BIM", D. Toullec, et al., J. Biol. Chem. 266, 15771–15781 (1991)), and compared the resulting nociceptive thresholds with those recorded following successive injections of the εV1-2 peptide and epinephrine. Because BIM inhibits epinephrine-induced hyperalgesia to a similar extent as εV1-2 (FIG. 10D), PKCε appears to be the only PKC isozyme involved in epinephrine-induced hyperalgesia.

Example 6

PKCε Acts in Primary Afferent Neurons

In order to determine the location(s) of PKCε's hyperalgesia-transducing activity, the cellular distribution of PKCε was examined. Anesthetized mice and rats were transcardially perfused with PBS (137 mM NaCl, 2.7 mM KCl, 1.47 mM $KH_2PO_4$, 8 mM $Na_2HPO_4$, 0.5 mM $MgCl_2$, 0.9 mM $CaCl_2$, pH 7.2) and then 4% paraformaldehyde in PBS. Spinal cords and DRGs were removed and placed in 4% paraformaldehyde for 3 hours, then in PBS-containing 20% sucrose for 24 hr and 40% sucrose for 24 hr. Sections (5–10 μm) were cut using a refrigerated microtome (Leica SM2000R), and treated with methanol:acetone (1:1) for 10 minutes at −20° C. DRG neurons were incubated at 25° C. in PBS/1% normal goat serum/0.05% Tween-20 for 1 hour, and then in the same buffer containing polyclonal anti PKCε (1:300 dilution, Santa Cruz Biotechnology) for 1–2 hours.

Sections were visualized using FITC-conjugated goat anti-rabbit IgG (1:50 dilution, Vector Laboratories, Burlingame, Calif.). For PKCε immunocytochemistry, spinal cord sections were pretreated with 3% $H_2O_2$ before incubation with 4% normal goat serum and 0.05% Tween-20 in Superblock (Pierce). Specimens were then incubated with polyclonal anti-PKCε antibody (1:300 dilution) overnight in PBS/1% Tween-20, and immunoreactivity was detected using the ABC kit (Vector) with diaminobenzamine followed by enhancement with 0.02% osmium tetroxide.

PKCε was present in 70±2% of the DRG neurons in wild-type adult mice (n=6), including most small- and many medium-diameter DRG neurons (FIGS. 11A and C). In rats, similar size DRG neurons express PKCε (FIG. 10A).

Since nociceptive DRG neurons terminate in the dorsal horn of the spinal cord, PKCε distribution was also examined in the spinal cords of wild-type and PKCε-mutant mice. In normal mouse (n=4) spinal cords, PKCε was detected in the superficial dorsal horn (FIG. 3D). Thus, PKCε is present in primary afferent nerve fibers of DRG neurons. In PKCε-mutant mice, no PKCε was detected in the spinal cord (FIG. 11B).

To address the possibility that intradermal injection of the εV1-2 peptide or BIM blocked hyperalgesia by inhibiting PKCε in non-neuronal cells residing in the dermis, the skin of normal rats was stained with a PKCε antibody. PKCε was detected in a thin band in the basal layer of the epidermis, but no PKCε was detectable in the dermis. Preabsorption of the anti-PKCε antibody with the immunizing peptide eliminated the staining, demonstrating that it is specific. These results indicate that, since no PKCε is present in the dermis, intradermally injected PKCε inhibitors do not act by inhibiting PKCε in dermal connective tissue. Rather, these data combined with those presented above lead to the conclusion that PKCε inhibitors injected into the dermis enter primary afferent neurons (small- and medium-diameter DRG neurons) and act on the PKCε present in these cells.

PKCε immunoreactivity was present in small and medium sized DRG neurons and in the superficial laminae of the dorsal horn of the spinal cord where nociceptive afferents terminate. Moreover, intradermal injection of a PKCε inhibitor peptide reduced epinephrine-induced hyperalgesia; this peptide was injected after the injection of hypotonic solution, an effective method for introducing peptides into peripheral nerve endings (L. K. West, L. Huang, *Biochemistry* 19, 4418–4423 (1980)). Since other cell types in the dermis did not express PKCε, these results indicate that PKCε residing in DRG neurons is necessary for the hyperalgesic effect of epinephrine.

Example 7

PKCε Modulates Acute and Chronic Chemotherapy-Induced Neuropathic Pain

Humans undergoing chemotherapy frequently experience hyperalgesia. Vincristine is a chemotherapeutic drug known to cause such hyperalgesia, and a rat model of vincristine-induced hyperalgesia was established as follows. Vincristine (100 μg/kg in saline; Sigma Chemical Catalog) was administered intravenously daily to each of 32 rats over a period of two weeks. After the second day of vincristine administration, the rats demonstrated an acute dose-dependent decrease in mechanical nociceptive thresholds and an increased response ("hyperalgesia") to non-noxious mechanical stimuli, administered by Ugo Basile analgesymeter, relative to control rats but did not show any significant motor deficits (as measured by Rotorod analysis). During the second week of vincristine administration, vincristine-treated rats displayed lowered chronic mechanical nociceptive thresholds and increased response to non-noxious mechanical stimuli 24 hours after the most recent vincristine treatment. Responses to mechanical stimuli gradually decreased to baseline during the two weeks following discontinuation of vincristine treatment.

To determine whether administration of an inhibitor of PKCε would lessen vincristine-induced hyperalgesia in the rat model described above, on the 13th day of vincristine treatment, rats received no treatment (n=16) or intradermal injections of sterile water followed by intradermal injections of either 1 μg εV1-2, a PKCε inhibitory peptide (n=8; labeled "PKCεI" on FIG. 12A), or 1 μg S-VεV1-2, a scrambled version of the εV1-2 peptide (n=8; labeled "PCKεI SCR" on FIG. 12A), 20–30 minutes before administration of a mechanical stimulus. As shown in FIG. 12A, vincristine-induced chronic hyperalgesia was significantly diminished by administration of the PKCε inhibitor (p<0.05) but unaffected by the scrambled inhibitor peptide. These data demonstrate that inhibition of PKCε lessens pain due to toxic nerve injury, such as that induced by a chemotherapeutic drug.

Example 8

PKCε Modulates Pain Associated with Diabetic Neuropathy

Persons with uncontrolled or poorly controlled diabetes frequently experience hyperalgesia. The role of PKCε in diabetic neuropathy was examined in a model of diabetes in which male Sprague-Dawley rats receive subcutaneous injection of streptozotocin (70 mg/kg), a pancreatic β-cell toxin. These rats display hyperglycemia and glucosuria within 24 hours after the injection and show decreased nociceptive thresholds in response to mechanical stimuli administered by Ugo Basile analgesymeter in the hind paw after one week (Ahlgren, S. C. et al, *J. Neurophysiology*, 68, 2077–2085 (1992); Ahlgren, S. C. and Levine, J. D., *Neuroscience* 52, 1049–1055 (1993)). Four weeks after the streptozotocin injection, each rat received no treatment (n=8) or an intradermal injection of sterile water followed by a intradermal injections of (1) 1 μg bisindolymaleimide, a protein kinase C inhibitor (n=4; labeled "BIM" on FIG. 12B), (2) 1 μg εV1-2, a PKCε inhibitory peptide (n=8; labeled "PKCεI" on FIG. 12B), or (3) 1 μg S-VεV1-2, a scrambled version of the εV1-2 peptide (n=4; labeled "PCKεI SCR" on FIG. 12B) and were subsequently exposed to mechanical stimuli. As shown in FIG. 12B, administration of either bisindolymaleimide or εV1-2 markedly reduced the diabetes-induced decrease in nociceptive threshold (both p<0.05) but treatment with the scrambled peptide had little effect on the decrease in nociceptive threshold. These data demonstrate that PKCε is the major[1] isozyme of PKC that mediates hyperalgesia in diabetics and that administration of inhibitors of PKCε lessens pain associated with diabetic neuropathy.

[1] Since bisindolymaleimide caused somewhat greater reduction in the percentage decrease in nociceptive threshold than PKCεI, it is possible that one or more isozymes of PKC other than PKCε have roles in modulating diabetes-induced hyperalgesia.

Example 9

PKCε Modulates Hyperalgesia Induced by Traumatic Nerve Injury

The Seltzer traumatic nerve injury model (Seltzer, Z. et al, *Pain* 43, 205–218 (1990)) is used to investigate the role of PKCε in modulating hyperalgesia induced by traumatic nerve injury. After determining sites in the dorsal aspect of the hindpaw in which traumatic nerve injury has caused hyperalgesia, rats receive no treatment or intradermal injections of sterile water at such site followed by intradermal injections of (1) 1 μg bisindolymaleimide, (2) 1 μg εV1-2, or (3) 1 μg S-VεV1-2. Responses to mechanical stimuli are subsequently tested, and inhibitors of PKCε are shown to at least partially reverse hyperalgesia associated with traumatic nerve injury.

Example 10

PKCε Modulates Acute Inflammatory Pain

The acetic acid writhing experiments reported in Example 3 indicate that PKCε contributes to inflammatory pain. To investigate whether PKCε mediates hyperalgesia induced by other inflammatory agents, rats received intradernal 10 μl injections of a 1% solution of carrageenan, a potent irritant (Ferreira, S. H. et al, Nature 334, 698–700 (1988)) and three and a half hours later, the rats received no treatment (n=12; labeled "Car-4" on FIG. 13) or intradermal injections of sterile water followed by intradermal injections of either 1 μg εV1-2, a PKCε inhibitory peptide (n=6; labeled "εV" on FIG. 13), or 1 μg S-VεV1-2, a scrambled version of the εV1-2 peptide (n=6; labeled "S-εV" on FIG. 13). When mechanical stimuli were applied 30 minutes later, as shown in FIG. 13, the rats that received only carrageenan or both carrageenan and the scrambled peptide showed substantial hyperalgesia. By comparison, the rats that received carrageenan and the PKCε inhibitory peptide showed almost no mechanical hyperalgesia. These data demonstrate that administration of an inhibitor of PKCε significantly diminishes carrageenan-induced hyperalgesia.

Example 11

PKCε Modulates Chronic Inflammatory Pain
A. Model for Chronic Inflammatory Pain

In order to investigate the role, if any, of PKCε in chronic inflammatory pain, the following model system for chronic inflammatory pain was developed. Rats received intradermal hind paw injections of carrageenan, an inflammatory agent. For up to 3–4 days following carrageenan administration, the rats displayed mechanical hyperalgesia, as assessed by the Randall-Selitto paw-withdrawal test. This was considered an acute response to the carrageenan-induced inflammation. Although administration of Prostaglandin $E_2$ ("$PGE_2$"), 5-hydroxytryptamine ("5-HT," serotonin) or CGS-21680 (an adenosine $A_2$-selective receptor agonist) normally causes untreated rats (that is, rats that have not received carrageenan injections) to experience hyperalgesia lasting up to 6 hours, the hyperalgesia experienced by carrageenan-sensitized rats following administration of any one of these substances lasted up to 24 hours. This prolonged hyperalgesia was seen in such rats up to three weeks after the carrageenan injection. These data establish a model of chronic prolonged inflammatory pain and suggest that changes induced by acute inflammation persist for a long period of time.
B. PKCε Modulates Chronic Inflammatory Pain and Processes That Give Rise To It The role of protein kinase C enzymes generally and the PKCε isozyme in particular in modulating chronic inflammatory pain was tested by administering 1 μg bisindolymaleimide ("BIM," a nonselective PKCε inhibitor) or 1 μg εV1-2 (a peptide that selectively inhibits PKCε) several days after the carrageenan injection, and subsequently treating the rats with $PGE_2$ and measuring the resulting hyperalgesia. The prolonged $PGE_2$-induced hyperalgesia normally seen in carrageenan-sensitized rats was inhibited by administration of BIM or εV1-2. These data show that prolonged $PGE_2$-induced hyperalgesia is dependent on PKCε activity and demonstrate that administration of an inhibitor of PKCε lessens chronic enhanced pain due to prior inflammation.

To examine whether protein kinase C modulates the processes by which a brief inflammatory event causes prolonged hyperalgesia many days later, rats received carrageenan and 1 μg BIM injections at the same time. Hyperalgesia was measured 72 hours later, when the rats were treated $PGE_2$. Administration of BIM at the same time as carrageenan attenuated both the acute hyperalgesia normally induced by carrageenan exposure and the prolonged hyperalgesia normally observed when the rats are treated with $PGE_2$ 72 or more hours after carrageenan exposure. These data demonstrate that PKC modulates both acute and chronic hyperalgesia. Therefore, administration of an inhibitor of PKC either at approximately the same time as the inflammatory agent giving rise to chronic, prolonged hyperalgesia or at about the same time as the hyperalgesia-inducing stimulus can lessen such chronic hyperalgesia. Administration of εV1-2 in lieu of BIM confirmed that these effects are due to the PKCε isozyme and showed that administration of a selective inhibitor of PKCε immediately before, during or after an inflammatory event lessens both acute pain due to such an event and interferes with the mechanisms that lead to chronic pain following such an event.

Not only can inhibitors of PKCε interfere with acute and chronic hyperalgesia due to inflammation, but administration of εV1-7, a selective activator of PKCε, in lieu of carrageenan, produced acute hyperalgesia and prolonged $PGE_2$-induced hyperalgesia that was substantially similar to that observed following carrageenan administration. These data indicate that activation of PKCε alone can produce prolongation of $PGE_2$ hyperalgesia, that carrageenan acts via the PKCε pathway and that PKCε plays a central role in modulating both acute and chronic inflammatory pain.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of lessening pain, said method comprising: administering to a subject in need thereof, an effective amount of an inhibitor of the ε isozyme of protein kinase C (PKCε), wherein said inhibitor is a selective inhibitor of PKCε.

2. The method of claim 1, wherein said selective inhibitor is a peptide selected from the group consisting of: εV1-1, εV1-2, εV1-3, εV1-4, εV1-5 and εV1-6.

3. A method of lessening pain, said method comprising: administering to a subject in need thereof, an effective amount of an inhibitor of the ε isozyme of protein kinase C (PKCε), wherein said subject suffers chronic inflammatory pain.

4. A method of lessening pain, said method comprising: administering to a subject in need thereof, an effective amount of an inhibitor of the ε isozyme of protein kinase C (PKCε), wherein said subject suffers inflammatory pain due to a condition selected from the group consisting of: sunburn, osteoarthritis, colitis, carditis, dermatitis, myositis, neuritis and collagen vascular disease.

* * * * *

UNITED STATES PATENT AND TRADEMARK OFFICE
CERTIFICATE OF CORRECTION

| | |
|---|---|
| PATENT NO. | : 6,376,467 B1 |
| APPLICATION NO. | : 09/347370 |
| DATED | : April 23, 2002 |
| INVENTOR(S) | : Messing et al. |

Page 1 of 1

It is certified that error appears in the above-identified patent and that said Letters Patent is hereby corrected as shown below:

On the Title page, item (60) immediately below "Related U.S. Application Data," please revise as follows:

Delete "Provisional application No. 60/103,763, filed on Oct. 9, 1998, and provisional application No. 60/097,755, filed on Jul. 6, 1998."

and insert --Provisional application No. 60/103,763, filed on Oct. 9, 1998.--

Signed and Sealed this

Fifth Day of May, 2009

JOHN DOLL
*Acting Director of the United States Patent and Trademark Office*